(12) United States Patent
Jungles et al.

(10) Patent No.: US 9,457,067 B2
(45) Date of Patent: Oct. 4, 2016

(54) SIALYLATED GLYCOPROTEIN COMPOSITIONS AND USES THEREOF

(71) Applicant: Ultragenyx Pharmaceutical Inc., Novato, CA (US)

(72) Inventors: Steven Jungles, Naperville, IL (US); Gabrielle Morris, Novato, CA (US); Jeff Grubb, Petaluma, CA (US); Michael Vellard, San Rafael, CA (US); Emil D. Kakkis, San Rafael, CA (US)

(73) Assignee: Ultragenyx Pharmaceutical Inc., Novato, CA (US)

( * ) Notice: Subject to any disclaimer, the term of this patent is extended or adjusted under 35 U.S.C. 154(b) by 0 days.

(21) Appl. No.: 14/639,171

(22) Filed: Mar. 5, 2015

(65) Prior Publication Data

US 2015/0250860 A1     Sep. 10, 2015

Related U.S. Application Data

(60) Provisional application No. 61/948,421, filed on Mar. 5, 2014, provisional application No. 62/114,313, filed on Feb. 10, 2015.

(51) Int. Cl.
| | |
|---|---|
| *A61K 38/47* | (2006.01) |
| *C12N 9/24* | (2006.01) |
| *A61K 45/06* | (2006.01) |
| *C12N 9/38* | (2006.01) |

(52) U.S. Cl.
CPC .............. *A61K 38/47* (2013.01); *A61K 45/06* (2013.01); *C12N 9/2402* (2013.01); *C12N 9/2468* (2013.01); *C12Y 302/01031* (2013.01)

(58) Field of Classification Search
None
See application file for complete search history.

(56) References Cited

U.S. PATENT DOCUMENTS

| | | |
|---|---|---|
| 2011/0280856 A1 | 11/2011 | Selden et al. |
| 2015/0366951 A1 | 12/2015 | Jungles et al. |

FOREIGN PATENT DOCUMENTS

WO    WO 2015/134696    9/2015

OTHER PUBLICATIONS

Schröder et al., "Serum- and protein-free media formulations for the Chinese hamster ovary cell line DUKXB11", Journal of Biotechnology 108 (2004) 279-292.*
Brot et al., "Purification and Properties of B-Glucuronidase from Human Placenta", Biochemistry, 1978, 17(3):385-391.*
Bork et al., "Increasing the Sialylation of Therapeutic Glycoproteins: The Potential of the Sialic Acid Biosynthetic Pathway", Journal of Pharmaceutical Sciences, 2009, 98(10):3499-3508. DOI 10.1002/jps.*
Pastores et al., "Advances in the management of Anderson-Fabry disease: enzyme replacement therapy", Expert Opin. Biol. Ther. (2002) 2(3):325-333.*
International Search Report and Written Opinion for International Application No. PCT/US2015/018859, mailed Jun. 25, 2015, 12 pages.
Beuvery, E. C. et al., Animal Cell Technology: Developments Towards the 21st Century. n.p.: Kluwer Acad. Press, 1995. Bibliotheksverbund Bayern: [online] May 8, 2015, p. 404.
Lawton, A., "Endocrinologic & Metabolic Drugs," Advisory Committee Meeting, Fabrazyme (agalsidase beta), Powerpoint, Jan. 13, 2003, Accessed Online, <http://fda.gov/ohrms/dockets/ac/03/slides/3917S1_01_Genzyme.ppt>.
Lee, K. et al., "A biochemical and pharmacological comparison of enzyme replacement therapies for the glycolipid storage disorder Fabry disease," Glycobiology, 13(4):305-313 (2003).
Sando, G. N. et al., "Recognition and receptor-mediated uptake of a lysosomal enzyme, Alpha-L-Iduronidase, by cultured human fibroblasts," Cell [online], 12(3):619-627 (Nov. 1977), Retrieved from the Internet: <http://www.sciencedirect.com/science/article/pii/0092867477902628>, 2 pages.
Volger, C. et al., "Overcoming the blood-brain barrier with high-dose enzyme replacement therapy in murine mucopolysaccharidosis VII," PNAS, 102(41):14777-14782 (Oct. 2005).

* cited by examiner

*Primary Examiner* — Suzanne M Noakes
(74) *Attorney, Agent, or Firm* — Cooley LLP

(57) ABSTRACT

The present application relates to sialylated glycoprotein compositions and methods of their use in treating various conditions and disorders.

12 Claims, 9 Drawing Sheets

FIGURE 3, Continued
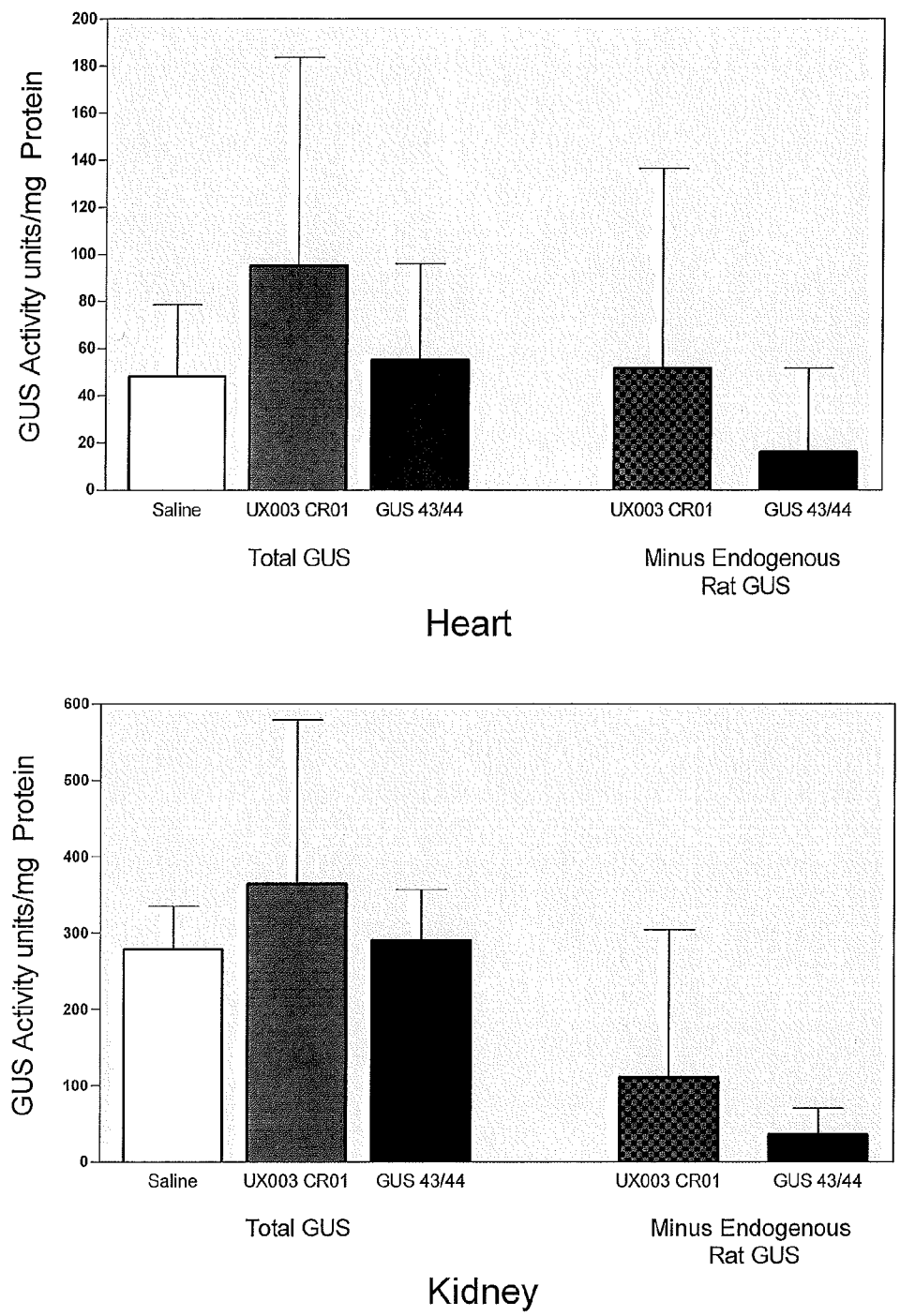

FIGURE 3, Continued
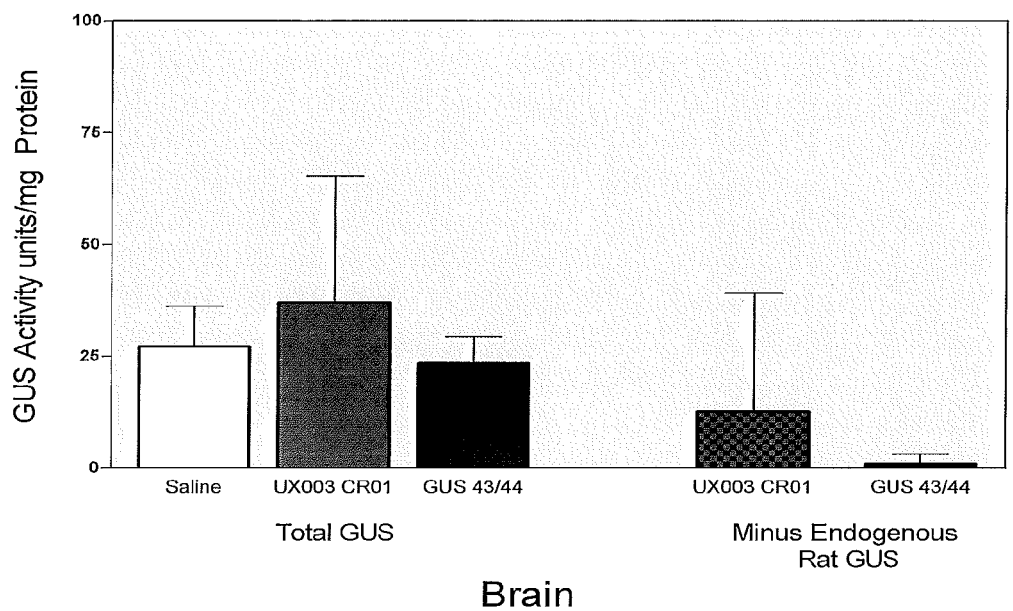
Brain
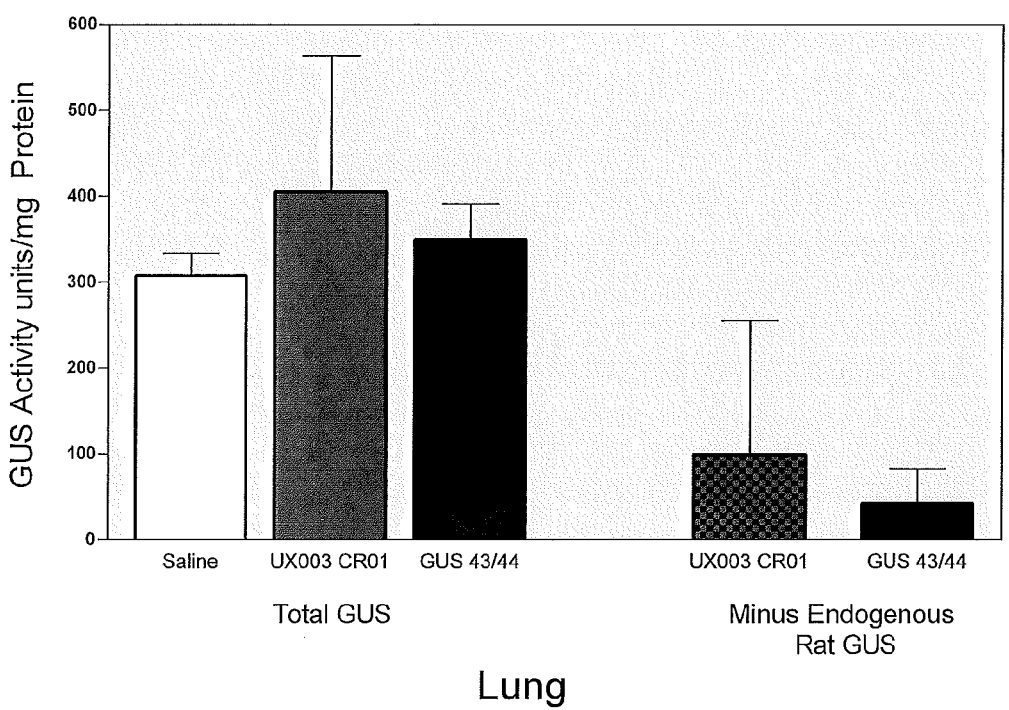
Lung

*Baseline scan was not determined (ND); subjectively radiologist reports no change at BL vs. week 12

SIALYLATED GLYCOPROTEIN COMPOSITIONS AND USES THEREOF

CROSS-REFERENCE TO RELATED APPLICATIONS

This application claims priority to U.S. Provisional Application Ser. No. 61/948,421, filed Mar. 5, 2014, and U.S. Provisional Application Ser. No. 62/114,313, filed Feb. 10, 2015, each of which is herein incorporated by reference in their entireties for all purposes.

FIELD OF THE INVENTION

The present invention relates to sialylated glycoprotein compositions and methods of their use in treating various conditions and disorders.

DESCRIPTION OF TEXT FILE SUBMITTED ELECTRONICALLY

The contents of the text file submitted electronically herewith are incorporated herein by reference in their entirety: A computer readable format copy of the Sequence Listing (filename: ULPI_020_02US_SeqList_ST25.txt, date recorded: Mar. 2, 2015, file size: 9 kilobytes).

BACKGROUND OF THE INVENTION

The number of commercially-available therapeutic proteins has increased dramatically in recent years and most of these proteins are glycoproteins. The presence of sialic acid in a glycoprotein can positively affect absorption, serum half-life, and clearance from the serum, as well as the physical, chemical and immunogenic properties of the respective glycoprotein. In certain circumstances, it may therefore be desirable to increase the sialic acid content of a glycoprotein intended for use in pharmacologic applications.

SUMMARY OF THE INVENTION

The present invention is based, in part, on the discovery that recombinant glycoprotein produced from mammalian cells through the use of serum/protein free media improves sialylation of the recombinant glycoprotein, e.g., without reducing the M6P content of the recombinant glycoprotein.

In some embodiments of the present invention, a composition comprises a recombinant glycoprotein having a sialic acid content greater than 0.05 mol/mol of the recombinant glycoprotein. In some embodiments, a composition comprises a recombinant glycoprotein having a sialic acid content greater than 0.1 mol/mol of the recombinant glycoprotein. In some embodiments, a composition comprises a recombinant glycoprotein having a sialic acid content greater than 0.5 mol/mol of the recombinant glycoprotein. In some embodiments, a composition comprises a recombinant glycoprotein having a sialic acid content greater than 0.7 mol/mol of the recombinant glycoprotein. In some embodiments, a composition comprises a recombinant glycoprotein having a sialic acid content greater than 1 mol/mol of the recombinant glycoprotein. In some embodiments, a composition comprises a recombinant glycoprotein having a sialic acid content greater than 1.5 mol/mol of the recombinant glycoprotein. In some embodiments, a composition comprises a recombinant glycoprotein having a sialic acid content greater than 2 mol/mol of the recombinant glycoprotein. In some embodiments, a composition comprises a recombinant glycoprotein having a sialic acid content greater than 5 mol/mol of the recombinant glycoprotein. In some embodiments, a composition comprises a recombinant glycoprotein having a sialic acid content greater than 10 mol/mol of the recombinant glycoprotein. In some embodiments, a composition comprises a recombinant glycoprotein having a sialic acid content greater than 20 mol/mol of the recombinant glycoprotein.

In some embodiments, the present invention provides a composition comprising a recombinant glycoprotein, wherein at least 10%, 20%, 30%, 40%, 50%, 60%, 70%, 80%, or 90% of galactose residues of the recombinant glycoprotein are sialylated.

In some embodiments, the present invention provides a composition comprising a recombinant glycoprotein, wherein the recombinant glycoprotein is human β-glucuronidase and has a sialylation content of at least 0.7 mol/mol of the recombinant glycoprotein.

In some other embodiments, the present invention provides a composition comprising a recombinant glycoprotein, wherein the recombinant glycoprotein is human β-glucuronidase and has a sialylation content of at least 0.7 mol/mol of the recombinant glycoprotein and a high level of mannose-6-phosphate (M6P) moieties.

In one embodiment, the present invention provides a composition comprising a recombinant glycoprotein, wherein the recombinant glycoprotein is human β-glucuronidase and has a sialylation content of at least 0.7 mol/mol of the recombinant glycoprotein and a high level of mannose-6-phosphate (M6P) moieties of at least 10 mol % of the total glycan of the recombinant glycoprotein.

In another embodiment, the present invention provides a composition comprising a recombinant glycoprotein, wherein the recombinant glycoprotein is human β-glucuronidase and has a sialylation content of at least 0.7 mol/mol of the recombinant glycoprotein and a high level of mannose-6-phosphate (M6P) moieties, e.g., K uptake is at its 60%, 70%, 80%, 90% or maximum such as from about 1 nM to about 3 nM when tested in human fibroblast cells (MPS7).

In yet another embodiment, the present invention provides a composition comprising a recombinant glycoprotein, wherein the recombinant glycoprotein is human β-glucuronidase and has a sialylation content of at least 0.7 mol/mol of the recombinant glycoprotein and a high level of mannose-6-phosphate (M6P) moieties, e.g., half-maximal uptake in human fibroblast cells such as concentrations at which the glycoprotein (e.g., human β-glucuronidase) reaches 50% of maximal uptake is about no more than 1 nM, 2 nM, 3 nM, 4 nM, or 5 nM.

In some embodiments, the present invention provides a preparation of a population of a recombinant glycoprotein, wherein at least 50 percent of the population is sialylated. In some embodiments, the present invention provides a preparation of a population of a recombinant glycoprotein, wherein at least 60 percent of the population is sialylated. In some embodiments, the present invention provides a preparation of a population of a recombinant glycoprotein, wherein at least 70 percent of the population is sialylated. In some embodiments, the present invention provides a preparation of a population of a recombinant glycoprotein, wherein at least 80 percent of the population is sialylated. In some embodiments, the present invention provides a preparation of a population of a recombinant glycoprotein, wherein at least 90 percent of the population is sialylated.

Also provided is a method of making a composition/preparation according to the present invention. In some embodiments, the method comprises expressing the recombinant glycoprotein in a cell culture with a serum or protein free media. In some embodiments, a protein-free, chemically defined media may be used to grow cells. In some embodiments, the media do not include an effective amount of a sugar selected from galactose, fructose, n-acetyl-mannosamine, mannose and combinations thereof. For example, the effective amount of a sugar is greater than 0.01 mM, 0.05 mM, or 0.1 mM.

In some embodiments, a cell culture comprises a mammalian cell. Exemplary mammalian cells include but are not limited to Chinese Hamster Ovary (CHO), HeLa, VERO, BHK, Cos, MDCK, 293, 3T3, myeloma (e.g. NSO, NSI), or WI38 cells. In a specific embodiment, the mammalian cells are Chinese Hamster Ovary (CHO) cells.

In some other embodiments, a cell culture comprises a plant cell. Exemplary plant cells include but are not limited to carrot cells or any other plant cell based cell culture, e.g., developed for recombinant protein production.

Further provided is a method of treating lysosomal storage disorder (LSD) comprising administering to an individual in need of such treatment a therapeutically effective amount of the composition/preparation as described herein. In an exemplary embodiment, the composition/preparation comprises recombinant human β-glucuronidase. In a further exemplary embodiment, the LSD is mucopolysaccharidosis type 7 (i.e., MPS 7, MPS VII, or Sly Syndrome). In some embodiments, the recombinant human β-glucuronidases provided herein have increased sialic acid content and are particularly useful in treating a LSD, e.g., MPS 7.

In some embodiments, the present invention provides a method for treating a lysosomal storage disorder (LSD) in a subject, comprising administering a regimen of the composition/preparation as described herein, wherein the administration provides a statistically significant therapeutic effect for the treatment of the LSD. In an exemplary embodiment, the composition/preparation comprises recombinant human β-glucuronidase. In a further exemplary embodiment, the LSD is MPS 7.

DEFINITIONS

As used herein, the term "effective" (e.g., "an effective amount") means adequate to accomplish a desired, expected, or intended result. An effective amount can be a therapeutically effective amount. A "therapeutically effective amount" refers to the amount of an active ingredient that, when administered to a subject, is sufficient to effect such treatment of a particular disease or condition. The "therapeutically effective amount" will vary depending on, e.g., the disease or condition, the severity of the disease or condition, and the age, weight, etc., of the subject to be treated.

In general, "treating" or "treatment" of any condition, disease or disorder refers, in some embodiments, to ameliorating the condition, disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to inhibiting the condition, disease or disorder, either physically, (e.g., stabilization of a discernible symptom), physiologically, (e.g., stabilization of a physical parameter) or both. In some embodiments, "treating" or "treatment" refers to delaying the onset of a condition, disease, or disorder.

Following long-standing patent law convention, the terms "a", "an", and "the" refer to "one or more" when used in this application, including the claims. The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" is used to indicate that a value includes the standard deviation of error for the device or method being employed to determine the value.

A glycoprotein, as used herein, is a protein that has been modified by the addition of one or more carbohydrates, including, especially, the addition of one or more sugar residues.

As used herein, "GUS" refers to β-glucuronidase, an exemplary glycoprotein in accordance with the present invention.

Sialylation, as used herein, is the addition of a sialic acid residue to a protein, which may be a glycoprotein. The term sialic acid, as used herein, encompasses a family of sugars containing 9 or more carbon atoms, including a carboxyl group. A generic structure encompassing all known natural forms of sialic acid is shown below.

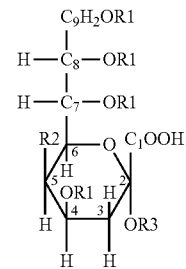

R1 groups at various positions on a single molecule can be the same as or different from each other. R1 can be a hydrogen or an acetyl, lactyl, methyl, sulfate, phosphate, anhydro, sialic acid, fucose, glucose, or galactose group. R2 can be an N-acetyl, N-glycolyl, amino, hydroxyl, N-glycolyl-O-acetyl, or N-glycolyl-O-methyl group. R3 represents the preceding sugar residue in an oligosaccharide to which sialic acid is attached in the context of a glycoprotein. R3 can be galactose (connected at its 3, 4, or 5 position), N-acetyl-galactose (connected at its 6 position), N-acetyl-glucose (connected at its 4 or 6 position), sialic acid (connected at its 8 or 9 position), or 5-N-glycolyl-neuraminic acid. Essentials of Glycobiology, Ch. 15, Varki et al., eds., Cold Spring Harbor Laboratory Press, New York (1999). More than 40 forms of sialic acid have been found in nature. Essentials of Glycobiology, Ch. 15, Varki et al., eds., Cold Spring Harbor Laboratory Press, New York (1999). A common form of sialic acid is N-acetylneuraminic acid (NANA), in which R1 is a hydrogen at all positions and R2 is an N-acetyl group.

DETAILED DESCRIPTION OF THE INVENTION

Figure 1:
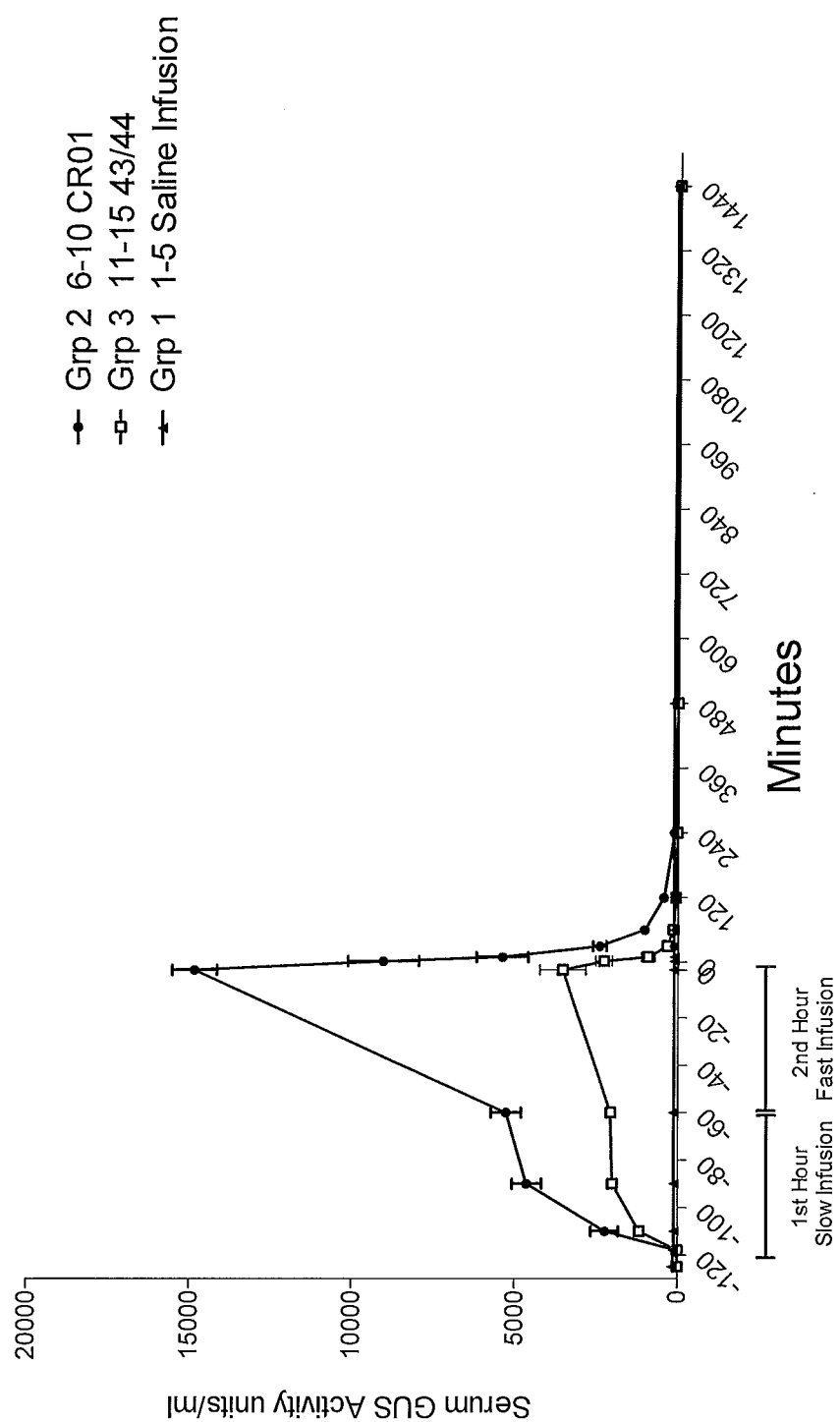
FIG. 1 is a plot comparing pharmacokinetics of recombinant human β-glucuronidases, GUS CR01 vs. GUS Lot 43/44 in rats via a two-stage infusion. The data show that the infusion with the higher sialylated CR01 results in less rapid clearance and a higher mean concentration during the infusion, which increases the total exposure to the enzyme, potentially enhancing its penetration of tissues that are more difficult to treat.

The present invention is based, in part, on the discovery that recombinant glycoprotein produced from mammalian cells through the use of serum/protein free media improves sialylation of the recombinant glycoprotein, and additionally levels of mannose-6-phosphate moieties of the recombinant glycoprotein.

Sialylated Glycoprotein Compositions

Compositions as described herein comprise one or more glycoproteins that have a high level or increased sialic acid content.

Sialic acids represent a family of aminosugars with 9-carbons with over 50 members derived from N-acetyleuraminic acid. Sialic acid is only one component out of several monosaccharides building glycans of glycoproteins, but has an outstanding impact on the quality and stability of any therapeutic glycoproteins for several reasons: (I) terminal galactose residues are one of the major factors determining the serum half-life of glycoproteins. The serum half-life is regulated by the expression of liver asialo-glycoprotein receptors. These receptors bind nonsialylated glycoproteins and bound asialo-glycoproteins are removed from the serum by endocytosis. As a consequence, expression of terminal sialic acid on galactose residues prevents serum glycoproteins from degradation; (II) sialic acids are important for masking antigenic determinants or epitopes. It is known that the receptors of the immune system (T- and B-cell receptors) often prefer nonsialylated structures. Therefore, the possibility of the generation of antibodies against the therapeutic glycoproteins correlates with the degree of its sialylation; (III) negatively charged sialic acids influence protein-specific parameters such as the thermal stability, the resistance to proteolytic degradation or its solubility (Bork et al., Increasing the Sialylation of Therapeutic Glycoproteins: The potential of the Sialic Acid Biosynthetic Pathway, Journal of Pharmaceutical Sciences, Vol. 98, No. 10, October 2009).

In one aspect, the invention provides compositions comprising a recombinant glycoprotein having a sialic acid content greater than 0.05 mol/mol, 0.1 mol/mol, 0.5 mol/mol, 0.7 mol/mol, 1 mol/mol, 1.5 mol/mol, 2 mol/mol, 5 mol/mol, 10 mol/mol or 20 mol/mol of the recombinant glycoprotein. In some embodiments, the invention provides compositions comprising a recombinant glycoprotein having a sialic acid content greater than 0.5 mol/mol of the recombinant glycoprotein. In additional embodiments, the invention provides compositions comprising a recombinant glycoprotein having a sialic acid content greater than 0.7 mol/mol of the recombinant glycoprotein. In certain additional embodiments, the invention provides compositions comprising a recombinant glycoprotein having a sialic acid content greater than 1 mol/mol of the recombinant glycoprotein.

In certain embodiments, the recombinant glycoprotein is a recombinant form of human β-glucuronidase, an enzyme responsible for catalyzing the hydrolysis of β-D-glucuronic acid residues from the non-reducing end of mucopolysaccharides. In some embodiments, the recombinant human β-glucuronidase (rhGUS) has a sialic acid content greater than 0.1 mol/mol, 0.5 mol/mol, 0.7 mol/mol, 1 mol/mol, 1.5 mol/mol, 2 mol/mol, or 5 mol/mol of the rhGUS. In one exemplary embodiment, the recombinant human β-glucuronidase (rhGUS) has a sialic acid content greater than 0.7 mol/mol of the rhGUS. In another exemplary embodiment, the recombinant human β-glucuronidase (rhGUS) has a sialic acid content greater than 1.0 mol/mol of the rhGUS. In yet another exemplary embodiment, the recombinant human β-glucuronidase (rhGUS) has a sialic acid content of about 1.2 mol/mol of the rhGUS.

In some embodiments, the recombinant human β-glucuronidase (rhGUS) has a sialic acid content of about 0.5 mol/mol to about 2.0 mol/mol of the rhGUS. In one embodiment, the recombinant human β-glucuronidase (rhGUS) has a sialic acid content of about 0.6 mol/mol to about 1.5 mol/mol of the rhGUS. In another embodiment, the recombinant human β-glucuronidase (rhGUS) has a sialic acid content of about 0.7 mol/mol to about 1.4 mol/mol of the rhGUS. In an exemplary embodiment, the recombinant human β-glucuronidase (rhGUS) has a sialic acid content of about 0.8, mol/mol to about 1.3 mol/mol of the rhGUS. In another exemplary embodiment, the recombinant human β-glucuronidase (rhGUS) has a sialic acid content of about 1.0 mol/mol to about 1.2 mol/mol of the rhGUS.

In some embodiments, the composition of the present invention includes a recombinant glycoprotein having at least 10%, 20%, 30%, 40%, 50%, 60%, 70%, 80% or 90% of sites suitable for sialic acid linkage sialylated. In general, galactose is the site suitable for sialic acid linkage or sialylation. In certain embodiments, a composition comprises a recombinant glycoprotein, wherein at least 10%, 20%, 30%, 40%, 50%, 60%, 70%, 80%, or 90% of the galactose residues of the recombinant glycoprotein are sialylated. In some embodiments, the composition comprises a recombinant glycoprotein, wherein at least 50% of the galactose residues of the recombinant glycoprotein are sialylated. In additional embodiments, the composition comprises a recombinant glycoprotein, wherein at least 60% of the galactose residues of the recombinant glycoprotein are sialylated. In certain additional embodiments, the composition comprises a recombinant glycoprotein, wherein at least 70% of the galactose residues of the recombinant glycoprotein are sialylated.

In certain embodiments, the recombinant glycoprotein is a recombinant human β-glucuronidase (rhGUS). In some embodiments, at least 40%, 50%, 60%, 70%, or 80% of the galactose residues of the recombinant human β-glucuronidase (rhGUS) are sialylated. In one exemplary embodiment, at least 50% of the galactose residues of the rhGUS are sialylated. In another exemplary embodiment, at least 60% of the galactose residues of the rhGUS are sialylated. In yet another exemplary embodiment, at least 70% of the galactose residues of the rhGUS are sialylated. In yet another exemplary embodiment, about 70%, 71%, 72%, 73%, 74%, or about 75% of the galactose residues of the rhGUS are sialylated.

In some embodiments, at least about 40% to at least about 90% of the galactose residues of the recombinant human β-glucuronidase (rhGUS) are sialylated. In one embodiment, at least about 50% to at least about 80% of the galactose residues of the recombinant human β-glucuronidase (rhGUS) are sialylated. In another embodiment, at least about 60% to at least about 80% of the galactose residues of the recombinant human β-glucuronidase (rhGUS) are sialylated. In an exemplary embodiment, at least about 65% to at least about 75% of the galactose residues of the recombinant human β-glucuronidase (rhGUS) are sialylated In another aspect, the invention provides compositions comprising a recombinant glycoprotein having a high level of sialic acid content as well as a high level of mannose-6-phosphate (M6P) moieties. As used herein, M6P moieties include any mannose-6-phosphate capable of binding to or being recognized by M6P receptors including without any limitation mono-phosphorylated and bis-phosphorylated mannose-6-phosphate. In one embodiment, M6P moieties include any M6P binding to cation-independent M6P receptor (CI-MPR). In another embodiment, M6P moieties include any M6P binding to cation-dependent M6P receptor (CD-MRP). In yet another embodiment, M6P moieties include any bis-phosphorylated M6P.

According to the present invention, a high level of mannose-6-phosphate moieties can include any level of M6P moieties that is considered high by one skilled in the art, e.g., measured using any suitable means known to or later developed by one skilled in the art. In one embodiment, a high level of M6P moieties of a recombinant glycoprotein includes M6P moiety levels of at least 10 mol %, 11 mol %, 12mol %, 13 mol %, 14 mol % or 15 mol % of the total glycan of the recombinant glycoprotein. For example, the recombinant glycoprotein can have a high level of M6P as determined by the percentage of M6P peak area over total glycan peak area, e.g., at least 10%, 11%, 12%, 13%, 14% or 15%. In some embodiments, the recombinant glycoprotein is a recombinant human β-glucuronidase (rhGUS) and comprises M6P moiety levels of at least 10 mol %, 11 mol %, 12mol %, 13 mol %, 14 mol % or 15 mol % of the total glycan of the rhGUS. In an exemplary embodiment, the rhGUS comprises M6P moiety levels of about 13% to about 15%.

In another embodiment, a high level of M6P moieties of a recombinant glycoprotein includes a high level of uptake of the recombinant glycoprotein by human cells, e.g., high affinity uptake amount by human fibroblast cells. For example, the recombinant glycoprotein can have a M6P dependent K uptake of no more than 1 nM, 1.1 nM, 1.2 nM, 1.3 nM, 1.4 nM, 1.5 nM, 1.6 nM, 1.7 nM, 1.8 nM, 1.9 nM, 2 nM, 2.1 nM, 2.2 nM, 2.3 nM, 2.4 nM, 2.5 nM, 2.6 nM, 2.7 nM, 2.8 nM, 2.9 nM, 3 nM, 4 nM, or 5 nM by any suitable human cells, e.g., human fibroblast cells. In some embodiments, the recombinant glycoprotein is a recombinant human β-glucuronidase (rhGUS) and has a M6P dependent K uptake of less than 5 nM, less than 4 nM, less than 3 nM, or less than 2 nM. In an exemplary embodiment, the rhGUS has a M6P dependent K uptake of about 1.2 nM to about 1.8 nM.

In yet another embodiment, a high level of M6P moieties in a recombinant glycoprotein includes lower concentrations required to achieve maximum uptake of the recombinant glycoprotein by human cells, e.g., lower half-maximum concentration. For example, the recombinant glycoprotein can achieve maximum uptake by human cells, e.g., fibroblast cells at concentrations less than 10 nM, 9 nM, 8 nM, 7 nM, 6 nM, 5 nM, 4 nM, 3 nM, 2 nM or 1 nM. In some embodiments, the recombinant glycoprotein is a recombinant human β-glucuronidase (rhGUS) can achieve maximum uptake by human cells, e.g., fibroblast cells at concentrations of less than 5 nM, less than 4 nM, less than 3 nM, or less than 2 nM. In an exemplary embodiment, the rhGUS can achieve maximum uptake by human cells, e.g., fibroblast cells at concentrations of about 1.2 nM to about 1.8 nM.

In still another embodiment, a high level of M6P moieties in a recombinant glycoprotein includes one or more levels of M6P moieties corresponding to levels of M6P moieties associated with natural sialylation content of the recombinant glycoprotein, e.g., sialylation content of the recombinant glycoprotein prior to any means for enhancement such as using the methods disclosed in the present application.

According to the present invention, in some embodiments the recombinant glycoprotein, e.g., a recombinant human β-glucuronidase or any other lysosomal enzyme, has a sialylation content of at least 1 mol/mol and a high level of M6P moieties of at least 10 mol %, 11 mol %, 12 mol %, 13 mol %, 14 mol % or 15 mol % of the total glycan of the recombinant glycoprotein. In one embodiment, the recombinant glycoprotein, e.g., a recombinant human β-glucuronidase or any other lysosomal enzyme, has a sialylation content of at least 1 mol/mol and a high level of M6P moieties with an uptake of at least 1 nM, 1.1 nM, 1.2 nM, 1.3 nM, 1.4 nM, 1.5 nM, 1.6 nM, 1.7 nM, 1.8 nM, 1.9 nM or 2 nM by human cells, e.g., human fibroblast cells. In another embodiment, the recombinant glycoprotein, e.g., a recombinant human β-glucuronidase or any other lysosomal enzyme has a sialylation content of at least 1 mol/mol and a high level of M6P moieties with maximum uptake by human cells, e.g., human fibroblast cells at less than 10 nM, 9 nM, 8 nM, 7 nM, 6 nM, 5 nM, 4 nM, 3 nM, 2 nM, or 1 nM of the recombinant glycoprotein.

It yet another aspect, the invention provides a composition comprising a population of recombinant glycoproteins, wherein at least 50%, 60%, 70%, 80%, or 90% of the population is sialylated. In one embodiment, at least 50%, 60%, 70%, 80% or 90% of the population is recombinant glycoprotein in accordance to the present invention, e.g., with respect to sialylation content and M6P level.

The recombinant glycoprotein provided by the present invention can be any glycoprotein. Exemplary recombinant glycoproteins include those comprising amino acid sequences identical to or substantially similar to all or part of one of the following proteins: a Flt3 ligand (as described in WO 94/28391), a CD40 ligand (as described in U.S. Pat. No. 6,087,329), erythropoietin, thrombopoietin, calcitonin, leptin, IL-2, angiopoietin-2 (as described by Maisonpierre et al. (1997), Science 277(5322):55-60, incorporated herein by reference), Fas ligand, ligand for receptor activator of NF-kappa B (RANKL, as described in WO 01/36637), tumor necrosis factor (TNF)-related apoptosis-inducing ligand (TRAIL, as described in WO 97/01633), thymic stroma-derived lymphopoietin, granulocyte colony stimulating factor, granulocyte-macrophage colony stimulating factor (GM-CSF, as described in Australian Patent No. 588819), mast cell growth factor, stem cell growth factor (described in e.g. U.S. Pat. No. 6,204,363, incorporated herein by reference), epidermal growth factor, keratinocyte growth factor, megakaryote growth and development factor, RANTES, growth hormone, insulin, insulinotropin, insulin-like growth factors, parathyroid hormone, interferons including α interferons, γ interferons, and consensus interferons (such as those described in U.S. Pat. Nos. 4,695,623 and 4,897,471, both of which are incorporated herein by reference), nerve growth factor, brain-derived neurotrophic factor, synaptotagmin-like proteins (SLP 1-5), neurotrophin-3, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS). Descriptions of proteins that can be produced according to the inventive methods may be found in, for example, *Human Cytokines: Handbook for Basic and Clinical Research, Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991), all of which are incorporated herein by reference.

The recombinant glycoproteins of the present invention can include any lysosomal enzyme, especially any enzyme useful for enzyme replacement therapy (ERT). Examples of such enzymes include, without any limitation, acid alpha-glucosidase, acid beta-glucosidase or glucocerebrosidase, alpha-Galactosidase A, acid beta-galactosidase, beta-Hexosaminidase A, beta-Hexosaminidase B, acid sphingomyelinase, galactocerebrosidase, acid ceramidase, arylsulfatase, alpha-L-Iduronidase, Iduronate-2-sulfatase, heparan N-sulfatase, alpha-N-Acetylglucosaminidase, Acetyl-CoA, alpha-glucosaminide N-acetyltransferase, N-Acetylglucosamine-6-sulfate sulfatase, N-Acetylgalactosamine-6-sulfate sulfatase, Acid beta-galactosidase, Arylsulfatase B, acid alpha-mannosidase, acid beta-mannosidase, acid alpha-L-fucosidase, sialidase, and alpha-N-acetylgalactosaminidase.

In certain exemplary embodiments, the recombinant glycoprotein of the present invention is recombinant human β-glucuronidase (rhGUS). Human β-glucuronidase is a glycoprotein which contains up to 16 oligosaccharides per molecule including a variety of chains that are of the high mannose, complex and hybrid types.

Also described herein are isolated or purified glycoprotein polypeptides. For example, disclosed herein are isolated or purified rhGUS polypeptides. The disclosed isolated or purified rhGUS polypeptides can be used in one or more of the compositions or methods disclosed herein.

The rhGUS polypeptides can include the rhGUS peptide sequence as well as fragments thereof, natural variants thereof, and unnatural variants thereof. The rhGUS sequence is provided in SEQ ID NO: 1. Disclosed herein are isolated or purified polypeptides that consist of SEQ ID NO: 1. Also disclosed herein are isolated or purified polypeptides that comprise SEQ ID NO: 1, as well as fragments thereof. Fragments may be at least about 10, 20, 50, 100, 200, 300, 400, or 500, or more contiguous amino acids. Also disclosed herein are isolated or purified polynucleotides that consist of or comprise a polynucleotide sequence capable of encoding the amino acid sequence of SEQ ID NO: 1.

In some embodiments, the rhGUS polypeptide has a sialic acid content greater than 0.1 mol/mol, 0.5 mol/mol, 0.7 mol/mol, 1 mol/mol, 1.5 mol/mol, 2 mol/mol, or 5 mol/mol of the rhGUS polypeptide. In some embodiments, the rhGUS polypeptide has a sialic acid content of about 0.5 mol/mol to about 2.0 mol/mol of the rhGUS polypeptide. In one embodiment, the rhGUS polypeptide has a sialic acid content of about 0.6 mol/mol to about 1.5 mol/mol of the rhGUS polypeptide. In another embodiment, the rhGUS polypeptide has a sialic acid content of about 0.7 mol/mol to about 1.4 mol/mol of the rhGUS polypeptide. In an exemplary embodiment, the rhGUS polypeptide has a sialic acid content of about 0.8 mol/mol to about 1.3 mol/mol of the rhGUS polypeptide. In another exemplary embodiment, the rhGUS has a sialic acid content of about 1.0 mol/mol to about 1.2 mol/mol of the rhGUS polypeptide.

In additional embodiments, at least 40%, 50%, 60%, 70%, or 80% of the galactose residues of the rhGUS polypeptide are sialylated. In an exemplary embodiment, at least about 65% to at least about 75% of the galactose residues of the rhGUS polypeptide are sialylated.

As described herein, the glycoproteins of the invention may be produced recombinantly. A polynucleotide encoding a recombinant glycoprotein of the invention can be introduced into a recombinant expression vector. In an exemplary embodiment, the recombinant glycoprotein is rhGUS. Accordingly, the application also relates to a recombinant expression vector comprising a polynucleotide encoding rhGUS. In one embodiment, the rhGUS protein produced by the recombinant expression vector consists of or comprises SEQ ID NO: 1.

As is understood in the art, recombinant vectors can be expressed in a suitable host cell system using techniques well known in the art. Accordingly, the application also relates to a host cell comprising a polynucleotide encoding rhGUS. In one embodiment, the rhGUS protein produced by the host cell consists of or comprises SEQ ID NO: 1. Suitable host cells for expressing the rhGUS protein of the present invention can include any cell line that can glycosylate proteins, preferably a mammalian cell line that has been genetically engineered to express a protein. For example, Chinese hamster ovary (CHO), HeLa, VERO, BHK, Cos, MDCK, 293, 3T3, myeloma (e.g. NSO, NSI), or WI38 cells may be used. In an exemplary embodiment, the cells used to produce the recombinant glycoprotein are Chinese Hamster Ovary (CHO) cells.

It yet another aspect, the invention provides a formulation comprising one or more glycoproteins that have a high level or increased sialic acid content. Formulations in general include liquid forms (solutions) such as, but not limited to reconstituted lyophilizates, and solid forms such as, but not limited to lyophilized forms, gels, microencapsulated partilces and pastes. The formulations in accordance with some embodiments of the present invention can be combinations of liquid formulations, lyophilizates, and liquid solitions prepared from reconstituted lyophilizates used in combination with gel, partiles, or pastes.

In some embodiments, the formulation is a solution including an aqueous buffer and the recombinant glycoprotein. The buffer may include Sodium Phosphate (Na—Pi), histidine, arginine, glycylglycine, tartaric acid, malic acid, lactic acid, aspartic acid, succinic acid or any combination thereof. In an exemplary embodiment, the buffer includes Na—Pi and histidine. In another embodiment, the buffer includes na-Pi, histidine and arginine.

In some embodiments, the buffer further includes one or more other ingredients such as, but not limited to sidium chloride (NaCl), polyxyethylene (Tween-20), potassium chloride, and sorbitol (e.g., D-sorbitol). In an exemplary embodiment, the buffer includes Na—Pi, histidine, NaCl and Tween 20.

As is well appreciated in the art, the stability of proteins may be dependent upon the pH and/or the ionic strength of a formulation. According to some embodiments of the present invention, the pH of the formulation is about 9.0 to about 5.0, for example, about 7.5 to about 6.0. In some embodiments, the pH is about 9.0, about 8.0, about 7.5, about 7.0, about 6.5, about 6.0, about 5.5 or about 5.0. It was the present invention that first recognized that lower pH of a formulation would improve the stability of the recombinant glycoprotein. For example, Table 6 in Example 2 demonstrates the improved stability as measured by the percentage of tetramers when the pH was changed to 6.0 from 7.5.

Methods of Production

In yet another aspect, the present invention provides a method for increasing the sialylation of a glycoprotein and additionally the M6P level of a glycoprotein produced by a cell culture with a serum or protein free media.

In general, culture media can be divided into several subsets based on the level of defined media. For example, a culture media can be: 1) Serum-containing media (commonly 10-20% Fetal Bovine Serum (FBS)); 2) Reduced-serum media (commonly 1-5% FBS); 3) Serum-free media (synonymous with defined media); 4) Protein-free media (no protein but contains undefined peptides from plant hydrolysates); 5) Chemically-defined media (with only recombinant proteins and/or hormones); 6) Protein-free, chemically defined media (contains only low molecular weight constituents, but can contain synthetic peptides/hormones); and 7) Peptide-free, protein-free chemically defined media (contains only low molecular weight constituents).

In some embodiments of the present invention, a reduced-serum media may be used to grow cells for the expression of glycoproteins. In some embodiments of the present invention, a serum-free media may be used to grow cells for the expression of glycoproteins. In some embodiments, a protein-free media may be used to grow cells for the expression of glycoproteins. In some embodiments, a chemically defined media may be used to grow cells for the expression of glycoproteins. In some embodiments, a protein-free, chemically defined media may be used to grow cells as demonstrated in Example 1. Further in some other embodiments, a peptide-free, protein-free chemically defined media is used to grow cells for the expression of glycoproteins.

As is well understood in the art, serum-free media may contain undefined animal-derived products such as serum albumin (purified from blood), hydrolysates, growth factors, hormones, carrier proteins, and attachment factors. These undefined animal-derived products will contain complex contaminants, such as the lipid content of albumin. In contrast, chemically defined media is defined as all of the components being identified and having their exact concentrations known. In some embodiments, a chemically defined medium is entirely free of animal-derived components. In some embodiments, a chemically defined medium excludes FBS, bovine serum albumin (BSA), human serum albumin (HAS) or combinations thereof. To achieve this, chemically defined media is commonly supplemented with recombinant versions of albumin and growth factors, usually derived from rice or $E.$ $coli$, or synthetic chemical such as the polymer polyvinyl alcohol which can reproduce some of the functions of BSA/HSA.

In some embodiments, the protein free medium described herein does not contain any proteins or components of biological origin. The absence of proteins in the medium eliminates the risk from contamination with blood borne or other pathogens or non-human proteins. In addition, such protein free media are usually completely defined as to identity and quantity of all of its ingredients, which may provide unrivalled product consistency, superior product quality control profile and better product stability than protein-containing media.

In some embodiments, the medium used herein does not include an effective amount of a sugar selected from galactose, fructose, n-acetyl-mannosamine, mannose and combinations thereof. For example, the effective amount of a sugar is greater than 0.01 mM, 0.05 mM, or 0.1 mM.

In some embodiments, the present invention provides a method for culturing mammalian cells comprising growing in culture a mammalian cell to produce a protein, e.g., a glycoprotein, in a serum or protein free media. Suitable cells for practicing the present invention include any cell line that can glycosylate proteins, preferably a mammalian cell line that has been genetically engineered to express a protein. In some embodiments, cells are homogenous cell lines. Numerous suitable cell lines are known in the art. For example, Chinese hamster ovary (CHO), HeLa, VERO, BHK, Cos, MDCK, 293, 3T3, myeloma (e.g. NSO, NSI), or WI38 cells may be used. In an exemplary embodiment, the cells used to produce the recombinant glycoprotein are Chinese Hamster Ovary (CHO) cells.

In accordance with some embodiments of the present invention, particularly useful cells are CHO cells, which are widely used for the production of recombinant proteins, e.g. cytokines, clotting factors, and antibodies (Brasel et al. (1996), Blood 88: 2004-2012; Kaufman et al. (1988), J. Biol Chem 263:6352-6362; McKinnon et al. (1991), J Mol Endocrinol 6: 231-239; Wood et al. (1990), J. Immunol 145: 3011-3016). A dihydrofolate reductase (DHFR) -deficient mutant cell line (Urlaub et al. (1980), Proc. Natl. Acad. Sci. USA 77:4216-4220), such as DXB11 or DG-44, is useful because the efficient DHFR selectable and amplifiable gene expression system allows high level recombinant protein expression in these cells (Kaufman (1990), Meth. Enzymol. 185: 527-566). In addition, these cells are easy to manipulate as adherent or suspension cultures and exhibit relatively good genetic stability. CHO cells and recombinant proteins expressed in them have been extensively characterized and have been approved for use in clinical commercial manufacturing by regulatory agencies.

In some embodiments, cells are grown in a fed batch mode. A fed-batch process is defined as an operational technique where one or more nutrients (substrates) are added to a culture medium to increase growth and achieve a high cell density in a bioreactor. Generally, adding nutrients in a controlled manner has a positive effect on the culture's growth rate and production. In some embodiments, a cell concentration greater than $10^6$ cells/mL, $10^7$ cells/mL, $2\times10^7$ cells/mL, $5\times10^7$ cells/mL, or $10^8$ cells/mL in bioreactors can be achieved. In some embodiments, bioreactors used in the fed batch mode have a volume of at least 10 L, 20 L, 50 L, 80 L, 100 L, 250 L, 500 L or 1000 L. Cells can be grown either in suspension or adherent cultures. In an exemplary embodiment, cells are grown in suspension. Mammalian cells are preferred, and in a particular exemplary embodiment, the mammalian cells are Chinese hamster ovary cells.

Therapeutic Treatment

In yet another aspect, the invention provides methods of treating a condition or disorder comprising administering to an individual in need of such treatment a therapeutically effective amount of the composition/preparation as described herein.

Compositions/preparations as described herein can be used alone or together with any therapeutic agents/compositions for various purposes, such as in the treatment methods described herein. In this regard, the compositions/preparations can be pharmaceutically acceptable.

In some embodiments, the condition or disorder requiring treatment is associated with an enzyme deficiency. Enzyme deficiencies in cellular compartments such as the golgi, the endoplasmic reticulum, and the lysosome cause a wide variety of human diseases. For example, lysyl hydroxylase, an enzyme normally in the lumen of the endoplasmic reticulum, is required for proper processing of collagen; absence of the enzyme causes Ehlers-Danlos syndrome type VI, a serious connective tissue disorder. GnT II, normally found in the golgi, is required for normal glycosylation of proteins; absence of GnT II leads to defects in brain development.

In an exemplary embodiment, the condition or disorder associated with an enzyme deficiency is a lysosomal storage disorder (LSD). More than forty lysosomal storage diseases (LSDs) are caused, directly or indirectly, by the absence of one or more proteins in the lysosome. LSDs arise from abnormal metabolism of various substrates, including glycosphingolipids, glycogen, mucopolysaccharides and glycoproteins. The metabolism of the substrates normally occurs in the lysosome and the process is regulated in a stepwise process by various degradative enzymes. Therefore, a deficiency in any one enzyme activity can perturb the entire process and result in the accumulation of particular substrates. Listed below are a number of lysosomal storage disorders and the corresponding defective enzymes:

Pompe disease: Acid alpha-glucosidase
Gaucher disease: Acid beta-glucosidase or glucocerebrosidase
Fabry disease: alpha-Galactosidase A
GM1-gangliosidosis: Acid beta-galactosidase
Tay-Sachs disease: beta-Hexosaminidase A
Sandhoff disease: beta-Hexosaminidase B
Niemann-Pick disease: Acid sphingomyelinase
Krabbe disease: Galactocerebrosidase
Farber disease: Acid ceramidase
Metachromatic leukodystrophy: Arylsulfatase A
Hurler-Scheie disease: alpha-L-Iduronidase
Hunter disease: Iduronate-2-sulfatase
Sanfilippo disease A: Heparan N-sulfatase
Sanfilippo disease B: alpha-N-Acetylglucosaminidase
Sanfilippo disease C: Acetyl-CoA: alpha-glucosaminide N-acetyltransferase
Sanfilippo disease D: N-Acetylglucosamine-6-sulfate sulfatase
Morquio disease A: N-Acetylgalactosamine-6-sulfate sulfatase
Morquio disease B: Acid beta-galactosidase
Maroteaux-Lamy disease: Arylsulfatase B
Sly disease: beta-Glucuronidase
alpha-Mannosidosis: Acid alpha-mannosidase
beta-Mannosidosis: Acid beta-mannosidase
Fucosidosis: Acid alpha-L-fucosidase
Sialidosis: Sialidase
Schindler-Kanzaki disease: alpha-N-acetylgalactosaminidase In certain exemplary embodiments, the present invention provides a method of treating a LSD comprising administering to an individual in need of such treatment a therapeutically effective amount of the composition/preparation as described herein. In one exemplary embodiment, the composition/preparation comprises recombinant human β-glucuronidase. In another exemplary embodiment, the LSD is mucopolysaccharidosis type 7 (i.e., MPS 7, MPS VII, or Sly Syndrome), a disorder resulting from the deficiency of β-glucuronidase. In some embodiments, the recombinant human β-glucuronidase harbors an increased sialic acid content and is particularly useful in treating a LSD, e.g., MPS 7.

In some embodiments, the present invention provides a method for treating a condition or disorder in a subject, comprising administering a regimen of a composition/preparation as described herein, wherein the administration provides a statistically significant therapeutic effect for the treatment of the condition or disorder. In some embodiments, the subject is human. In some embodiments, the composition/preparation comprises a recombinant glycoprotein that harbors an increased sialic acid content. In an exemplary embodiment, the recombinant glycoprotein has a sialylation content of at least 0.7 mol/mol of the recombinant glycoprotein. In another exemplary embodiment, the recombinant glycoprotein has a sialylation content of at least 1 mol/mol of the recombinant glycoprotein. In some embodiments, the condition or disorder is associated with an enzyme deficiency. In an exemplary embodiment, the condition or disorder associated with an enzyme deficiency is a lysosomal storage disorder (LSD).

Accordingly, the present invention provides a method for treating a lysosomal storage disorder (LSD) in a subject, comprising administering a regimen of the composition/preparation as described herein, wherein the administration provides a statistically significant therapeutic effect for the treatment of the LSD. In an exemplary embodiment, the composition/preparation comprises a recombinant human β-glucuronidase that harbors an increased sialic acid content. In a further exemplary embodiment, the LSD is mucopolysaccharidosis type 7 (i.e., MPS 7, MPS VII, or Sly Syndrome).

According to the present invention, treatment of the LSD includes any form of treating the LSD, e.g., reducing any symptom of the LSD, reducing the severity of any symptom of the LSD, shortening the duration of one or more symptoms of the LSD, treating or inhibiting any cause or condition associated with the LSD, or reducing any clinical criteria or measurement of the degree or condition of the LSD.

According to the present invention, the recombinant human β-glucuronidase of the present invention is administered in a regimen for the treatment of a LSD. In one embodiment, the LSD is MPS 7. Such regimen includes dosage per administration, per day, per every two weeks, as well as number of doses per treatment cycle, or combinations thereof.

In general, the recombinant human β-glucuronidase (rhGUS) of the present invention can be administered at a dosage of from about 0.1 mg to 20 mg, 0.2 mg to 15 mg, 0.5 to 12 mg, 1 mg to 10 mg. 1.5 mg to 8 mg, 2 mg to 6 mg per kg. In some embodiments, the rhGUS is administered at a dosage of about 0.1 mg, 0.2 mg, 0.5 mg, 1 mg, 2 mg, 3 mg, 4 mg, 5 mg, 6 mg, 7 mg, 8 mg, 9 mg, 10 mg, 11 mg, or about 12 mg per kg. In an exemplary embodiment, the rhGUS is administered at a dosage of about 4 mg per kg. Dosages may be adjusted for the condition of each patient as well as other drugs taken by the patient.

In some embodiments, such dosage is administered hourly, daily, weekly (i.e., QW), every two weeks (i.e., QOW), or monthly.

In some embodiments, rhGUS is administered hourly, about every 1 to 24 hours, 1 to 20 hours, 1 to 16 hours, 1 to 12 hours, 1 to 8 hours, 1 to 6 hours, 1 to 4 hours, 1 to 2 hours or every hour. In some embodiments, rhGUS is administered about every 2, 3, 4, 5, or 6 hours, or is administered about every 10 minutes, 15 minutes, 30 minutes, 45 minutes or 60 minutes.

In some embodiments, rhGUS may be administered by continuous infusion. In some embodiments, rhGUS may be administered to the patient for treatment periods of at least about 2, 4, 6, 10, 12 hours, or longer, which may improve effectiveness in some embodiments. In some embodiments, rhGUS is administered by continuous infusion for 1 to 24 hours, 1 to 20 hours, 1 to 16 hours, 1 to 12 hours 1 to 10 hours, 1 to 8 hours, 1 to 6 hours, 1 to 4 hours to 1 to 2 hours. In some embodiments, rhGUS is administered by continues infusions for about 10 minutes, 15 minutes, 30 minutes, 45 minutes or 60 minutes. In some embodiments, rhGUS is administered by continuous infusion for about 1 hour, 2 hours, 3 hours, 4 hours, 5 hours, 6 hours, 7 hours, 8 hours, 10 hours, 12 hours, 24 hours or more. In an exemplary embodiment, rhGUS is administered by continuous infusion for about 4 hours. In some embodiments, the continuous infusion periods are separated by periods of non-infusion (i.e., periods where no rhGUS is administered). The infusion may be carried out by any suitable means, such as by minipump.

In some embodiments, rhGUS is administered about every 1 to 30 days, every 1 to 25 days, every 1 to 20 days, every 1 to 14 days, every 1 to 10 days, every 1 to 5 days or daily.

In some embodiments, rhGUS is administered for about 1 to 12 weeks, about 1 to 24 weeks, about 1 to 36 weeks, about 1 to 48 weeks, about 1 to 60 weeks, or about 1 to 72 weeks. In some embodiments, the rhGUS is administered for about 1 month, 4 months, 8 months, 12 months, 16 months, 20 months, or more. In some embodiments, the rhGUS is administered for about 1 year, 2 years, 5 years, 10 years, or more. In some embodiments, the rhGUS is administered permanently (i.e., long-term use).

The rhGUS may be provided in lyophilized form, and reconstituted with sterile (e.g., aqueous) diluent prior to administration. The rhGUS may be administered by any effective route, including by subcutaneous injection, intramuscular injection, intravenous injection or infusion, and orally. In certain exemplary embodiments, the rhGUS is administered by intravenous infusion. Generally, the scheduled dose of rhGUS may be administered as a single dose (e.g., injection), or may be spaced out over the course of 24 hours or less, for example, by continuous infusion or repeated injection of subdose, or the like or as described extensively herein. In one embodiment, the scheduled dose of rhGUS may be administered as a single injection or as multiple injections.

In one embodiment, the patient receives approximately every other weekly (i.e., QOW) administration of rhGUS, at a dose between about 0.5 and 12 mg (e.g., about 1, 2, 4, 8, or 12 mg) per kg to reduce the severity of the LSD. In an exemplary embodiment, the patient receives approximately every other weekly administration of rhGUS at a dose of about 4 mg per kg. The regimen may continue in some embodiments for 12, 24, 36, 48, or 60 weeks, or permanently (i.e., long-term use).

According to the present invention, the rhGUS used in methods of the present invention can be administered either alone or in combination with a standard of care for the LSD, or as part of treatment regimen involving the standard of care for the LSD. In some embodiments, patients may be administered prophylactic antihistamine prior to each infusion of rhGUS. In additional embodiments, patients may be administered an antipyretic medication (e.g., ibuprofen or acetaminophen) prior to each infusion of rhGUS.

According to some embodiments of the present invention, administration of rhGUS provides a statistically significant therapeutic effect. In one embodiment, the statistically significant therapeutic effect is determined based on one or more standards or criteria provided by one or more regulatory agencies in the United States, e.g., FDA or other countries. In another embodiment, the statistically significant therapeutic effect is determined based on results obtained from regulatory agency approved clinical trial set up and/or procedure.

In some embodiments, the statistically significant therapeutic effect is determined based on a randomized, placebo-controlled, blind-start, single-crossover clinical trial set up. In some embodiments, the statistically significant therapeutic effect is determined based on data from a clinical trial design whereby subjects are randomized to one of 4 groups, each representing a different treatment sequence at different pre-defined time points in a blinded manner. In some embodiments, the statistically significant therapeutic effect is determined based on data from a patient population of at least 4, 6, 8, 10, or 12 subjects. In an exemplary embodiment, the statistically significant therapeutic effect is determined based on data from a patient population of 12 subjects.

In some embodiments, the statistically significant therapeutic effect is determined based on a study involving 12 subjects randomized 1:1:1:1 to one of four treatment sequence groups to either start treatment with 4 mg/kg rhGUS every other week (i.e., QOW), or placebo and cross over to 4 mg/kg rhGUS QOW at different, pre-defined time points. In some embodiments, the statistically significant therapeutic effect is determined based on a study in subjects dosed with either 4 mg/kg rhGUS or placebo QOW for 48 weeks.

In some embodiments, the statistically significant therapeutic effect is determined based on a study wherein rhGUS is administered QOW by slow IV infusion over a period of approximately 4 hours. In some embodiments, patients are pre-medicated with prophylactic antihistamine (e.g., cetirizine or loratadine) prior to each infusion of rhGUS.

In some embodiments, the statistically significant therapeutic effect is determined by measuring urinary glycosaminoglycan (uGAG) levels as the primary endpoint. Extensive research conducted over the last 20 years on MPS disorders provides significant relevant scientific data that allows for the qualification of uGAG levels as a biomarker that is reasonably likely to predict clinical benefit. The disease process and mechanism of action for the rhGUS in MPS 7 are well understood and data from other similar MPS disorders with comparable enzyme replacement therapies (ERTs) have established that uGAG is a direct pathophysiological and readily measured marker of the MPS disease process and uGAG is a reasonable predictor of treatment effect and clinical benefit in MPS disorders. In an exemplary embodiment, the statistically significant therapeutic effect is determined based on the determination of uGAG levels a clinical study involving 12 subjects who have been treated with 4 mg/kg rhGUS or placebo QOW over a 48-week period.

In some embodiments, the statistically significant therapeutic effect is determined using secondary efficacy measures (i.e., secondary endpoints) such as a multi-domain responder index and an evaluation of individualized clinical response.

In some embodiments, the statistically significant therapeutic effect is determined using a multi-domain responder index, which combines independent multi-domain analyses to assure that the broader basis for efficacy can be assessed without the complexity of trying to construct qualified composite endpoints. In some embodiments, the multi-domain responder index provides an assessment of rhGUS efficacy across a broad spectrum of clinical characteristics commonly observed in MPS 7 patients.

In some embodiments, the statistically significant therapeutic effect is determined by evaluating individualized clinical response (ICR). This is a measure of each subject's response to treatment that is selected based on the relevance of the outcome measure to concerns that the subject/parent/caregiver has reported, the subject's ability to complete clinical outcome assessment reliably, and the extent of impairment for that individual. Use of an ICR enables evaluation of the clinical benefit of rhGUS by assessing change in a prespecified individualized clinical outcome that is deemed most relevant for each subject and then determining an overall response rate for the study population. In some embodiments, the secondary efficacy measures (i.e., secondary endpoints) may include the evaluation of treatment subjects for signs and symptoms of MPS7 that interfere most with the subject's daily life (i.e., clinical problem evaluation). In some embodiments, the evaluation may include testing of pulmonary function, testing of walking distance, testing of shoulder flexion range of motion, and testing of fine motor function.

In some embodiments, the statistically significant therapeutic effect is determined based on data with an alpha value of less than or equal to about 0.05, 0.04, 0.03, 0.02 or 0.01. In some embodiments, the statistically significant therapeutic effect is determined based on data with a confidence interval greater than or equal to 95%, 96%, 97%, 98% or 99%. In some embodiments, the statistically significant therapeutic effect is determined based on data with a p value of less than or equal to about 0.05, 0.04, 0.03, 0.02 or 0.01. In some embodiments, the statistically significant therapeutic effect is determined on approval of Phase III clinical trial of the compositions and methods provided by the present invention, e.g., by FDA in the US.

In general, statistical analysis can include any suitable method permitted by a regulatory agency, e.g., FDA in the US or China or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis.

In some embodiments, lysosomal storage biomarkers can be used for predicting treatment response and/or determining treatment efficacy. In some embodiments, urinary glycosaminoglycan (uGAG) levels can be measured and a reduction in uGAG levels employed as an indicator of positive treatment response. In some embodiments, elevated levels of the uGAG biomarker, which later decrease upon administration of rhGUS, is predictive of treatment response. In some embodiments, this information can be employed in determining a treatment regimen (as described herein) for the treatment of a lysosomal storage disorder (e.g., MPS 7) using rhGUS. As such, the present invention provides methods for determining a treatment regimen which includes detecting a decrease in the level of a LSD biomarker in a biological sample from a subject treated with rhGUS and determining a treatment regimen of the rhGUS based on a decrease in the level of one or more one or more LSD biomarkers in a biological sample. In some embodiments, the LSD biomarker is uGAG. In some embodiments, a decreased or reduced level of uGAG is indicative of treatment response and/or treatment efficacy of treatment with rhGUS. In some embodiments, reduction of uGAG levels to a predetermined standard level is indicative of better treatment prognosis with rhGUS.

EXAMPLES

Example 1

Production and Quantitation of Total Sialic Acid

The recombinant human β-glucuronidase (rhGUS) produced in accordance with the present invention was labeled GUS CR01. The recombinant protein is produced from Chinese Hamster Ovary (CHO) cells that have been engineered to express and secrete the enzyme into the culture medium using a bioreactor culture system.

Previous batches of β-glucuronidase (labeled as GUS Lot 43/44) have been produced using the same cell line by a process in which the cells are grown attached to microcarriers in a continuous perfusion system. Cells are generally expanded in growth media containing Fetal Bovine Serum (FBS). Afterward, FBS is washed out and replaced with media containing hydrolysates and supernatant was harvested in perfusion mode.

In contrast to the previously reported methods, GUS CR01 was produced in a culture system in which the cells are grown in suspension in a fed batch mode. Another difference is GUS CR01 was cultured only in chemically defined protein free medium as opposed to serum containing medium used previously.

A method for quantitation of total sialic acid in GUS was developed at the Rentchler Biotechnologie (RB) Quality Control department for release-testing of the GUS drug substance. In this method, sialic acid residues are released from the rhGUS glycan structures with acid hydrolysis. The released sialic acid is then labeled with OPD (O-phenylenediamine dihydrochloride) and analyzed by Reversed-Phase HPLC analysis (RP-HPLC). To date, Lot 43/44 and six RB-produced lots of rhGUS have been analyzed at RB for total sialic acid. These results (Table 1) are consistent with the result seen at GlycoSolutions.

TABLE 1

Results for Total Sialic Acid Analysis of GUS

| Lot GUS | Production Method | Sialic Acid (mol/mol GUS monomer) |
| --- | --- | --- |
| Lot 43/44 | Previously Reported | 0.04 |
| PR01 | In accordance with the present invention | 1.0 |
| PR02 | In accordance with the present invention | 0.7 |

TABLE 1-continued

Results for Total Sialic Acid Analysis of GUS

| Lot GUS | Production Method | Sialic Acid (mol/mol GUS monomer) |
|---|---|---|
| CR01 | In accordance with the present invention | 1.1 |
| GMP1 | In accordance with the present invention | 1.2 |
| GMP2 | In accordance with the present invention | 1.2 |
| GMP3 | In accordance with the present invention | 1.2 |

Example 2

Pharmacokinetics in Male Sprague Dawley Rats

In this Example, recombinant human β-glucuronidases produced in accordance with the present invention were compared to ones produced as previously reported in the art. The objective of this study was to evaluate the pharmacokinetics and tissue distribution of recombinant human β-glucuronidases administered intravenously as a single two hour infusion in male Sprague Dawley rats. The rate of infusion was ⅓ of the total volume for the first hour followed by ⅔ of the total volume in the second hour. This dosing regimen was designed to simulate the dosing regimen to be used in the patients.

Materials and Methods

Test Articles and Infusions

Three test articles were used in this study: 0.9% sodium chloride as the non-enzyme control, GUS CR01 and GUS Lot 43/44. Complete specifications for the test articles can be found in Table 2.

TABLE 2

Test Articles

| Test Article 1 | |
|---|---|
| Name: | 0.9% Sodium Chloride for Injection, USP (Saline) |
| Source: | Baxter Healthcare (Marion, NC) |
| Physical Properties: | Clear liquid |
| Identifier/Lot Number: | C883827 |
| Sterility Status: | Sterile |
| Storage Conditions: | Room temperature |
| Expiration Date | April 2014 |

| Test Article 2 | |
|---|---|
| Name: | GUS CR01 |
| Source: | Ultragenyx Pharmaceutical Inc. (Novato, CA) |
| Quantity: | ~32.5 mL |
| Concentration: | 2.0 mg/mL |
| GUS Activity units/ml | 10.75 Munits/ml |
| Specific Activity units/mg | 5.35 Munits/mg |
| Physical Properties: | Clear liquid |
| Identifier/Lot Number: | CR01 |
| Storage Conditions: | 2 to 8° C. |
| Expiration Date: | Not provided |

| Test Article 3 | |
|---|---|
| Name: | GUS Lot 43/44 |
| Source: | Ultragenyx Pharmaceutical Inc. (Novato, CA) |
| Quantity: | ~25 mL |
| Concentration: | 2.5 mg/mL* (2.18 mg/ml) |
| GUS Activity units/ml | 11.4 Munits/ml |
| Specific Activity units/mg | 5.23 Munits/mg |
| Physical Properties: | Clear liquid |
| Identifier/Lot Number: | 43/44 |
| Storage Conditions: | −60 to −80° C. |
| Expiration Date: | Not provided |

The test articles were infused into male Sprague-Dawley rats at a dose of ~2 mg/Kg body weight during a single infusion consisting of two 1 hour phases. One third of the dose was infused over the first hour and two thirds of the dose was infused during the second hour (Table 3).

TABLE 3

Rat Group Numbers, Dose and Infusion Rates

| Group # | Test Article | Gender | n | Dose Route | Dose Concentration (mg/mL) | Dose rate (mL/min) | Total Dose (mg/kg) | Actual Dose* (mg/kg) |
|---|---|---|---|---|---|---|---|---|
| 1 | Saline | M | 5 | iv | n/a | 1$^{st}$ hr: 0.99 2$^{nd}$ hour: 1.98 | n/a | n/a |
| 2 | GUS lot: CR01 | M | 5 | iv | 0.203 | 1$^{st}$ hr: 0.94 2$^{nd}$ hour: 1.87 | ~2[1] | ~2[1] |
| 3 | GUS lot: 43/44 | M | 5 | iv | 0.253 | 1$^{st}$ hr: 0.78 2$^{nd}$ hour: 1.57 | ~2[1] | ~1.7[1] |

[1]Dose was based on the average body weight of all five rats in each group.

*The dose for GUS Lot 43/44 was originally based on a protein value of 2.5 mg/ml determined by BCA assay. If the protein concentration was based on absorbance at OD 280 and an extinction coefficient of 2.12, the actual dose was 84.8% × 2 = 1.7 mg/Kg.

Blood samples were taken from each rat pre-treatment and then at intervals during the slow infusion, fast infusion and post infusion phases by the schedule outlined in Table 4. Blood was allowed to clot, serum was separated and stored frozen at −80° C. pending shipment on dry ice for analysis.

TABLE 4

Infusion and Bleed Schedule

| Stage | Nominal Interval |
|---|---|
| | Predose |
| Slow Infusion | 2 min post start of infusion |
| | 10 min post start of infusion |
| | 30 min post start of infusion |
| | 60 min post start of infusion |
| Fast Infusion | 120 min post start of infusion |
| Post Infusion | 2 min (post end of infusion) |
| | 10 min (post end of infusion) |
| | 30 min (post end of infusion) |
| | 60 min (post end of infusion) |
| | 120 min (post end of infusion) |
| | 240 min (post end of infusion) |
| | 480 min (post end of infusion) |
| | 24 hr (post end of infusion) |

GUS Activity in Serum

β-glucuronidase activity was determined as follows: 25 μL of serum diluted 1:4 to 1:300 in 0.1 M sodium acetate, pH 4.8, and 1 mg/mL crystalline BSA was mixed with 50 μL of 10 mM 4-MU-β-D-glucuronide substrate in 0.1 M sodium acetate, pH 4.8, 1 mg/mL crystalline BSA. All solutions were pre-warmed to 37° C. mixed then incubated at 37° C. for 30 minutes. The assays were stopped by the addition of 200 μL glycine carbonate, pH 10.5, and read on a Molecular Devices M2$^e$ plate reader at excitation/emission wavelengths of 366/446 nm. Activity was expressed as 1 unit=1 nmole 4MU released/mL/hr at 37° C.

GUS Activity in Tissues

Tissues were collected at necropsy and placed in cryovials, snap frozen in liquid nitrogen, and stored at −80° C. pending shipment on dry ice for analysis. The distribution of GUS activity in the tissues was assessed as follows. Whole or partial tissue specimens were thawed and combined with 10 to 20 volumes of 25 mM Tris, 140 mM NaCl, 1 mM phenylmethyl sulfonyl fluoride, pH 7.2. Tissue homogenates were prepared using a Kinematica Polytron homogenizer for 30 seconds on ice; the resultant homogenates were freeze/thawed once (at −80° C.) followed by sonication for 20 seconds with cooling on ice. A 25 μL total volume of each homogenate was assayed for β-glucuronidase using 4MU-β-glucuronide as described previously. Protein concentration of the homogenates was determined by the bicinchoninic acid method. Tissue β-glucuronidase levels were expressed as nmoles of 4MU hydrolyzed/hr/mg protein.

Results and Discussion

Pharmacokinetics of GUS CR01 vs. GUS Lot 43/44 in the Plasma

FIG. 1 shows the β-glucuronidase activity in the sera of rats from each infusion group during the slow infusion stage, the fast infusion stage and the post infusion stage. The curve for Group 1 infused with saline only, indicates the low endogenous level of rat β-glucuronidase that is present in the sera of these rats. The endogenous level has been subtracted from the values in the other two plots from the rats infused with enzyme.

The plots for both GUS CR01 and GUS Lot 43/44 show a time dependent increase in enzyme activity levels that reach a steady-state level by the end of the slow infusion period then increases again concomitant with the start of the fast infusion period. However in contrast, GUS CR01 reaches a level in the serum 2-fold higher at the end of the slow infusion and 3-fold higher at the end of the fast infusion period compared to GUS Lot 43/44. It can also be seen in FIG. 1 that the rapid clearance of both enzymes from the serum after the infusions cease which is characteristic for lysosomal enzymes in general.

Figure 2:
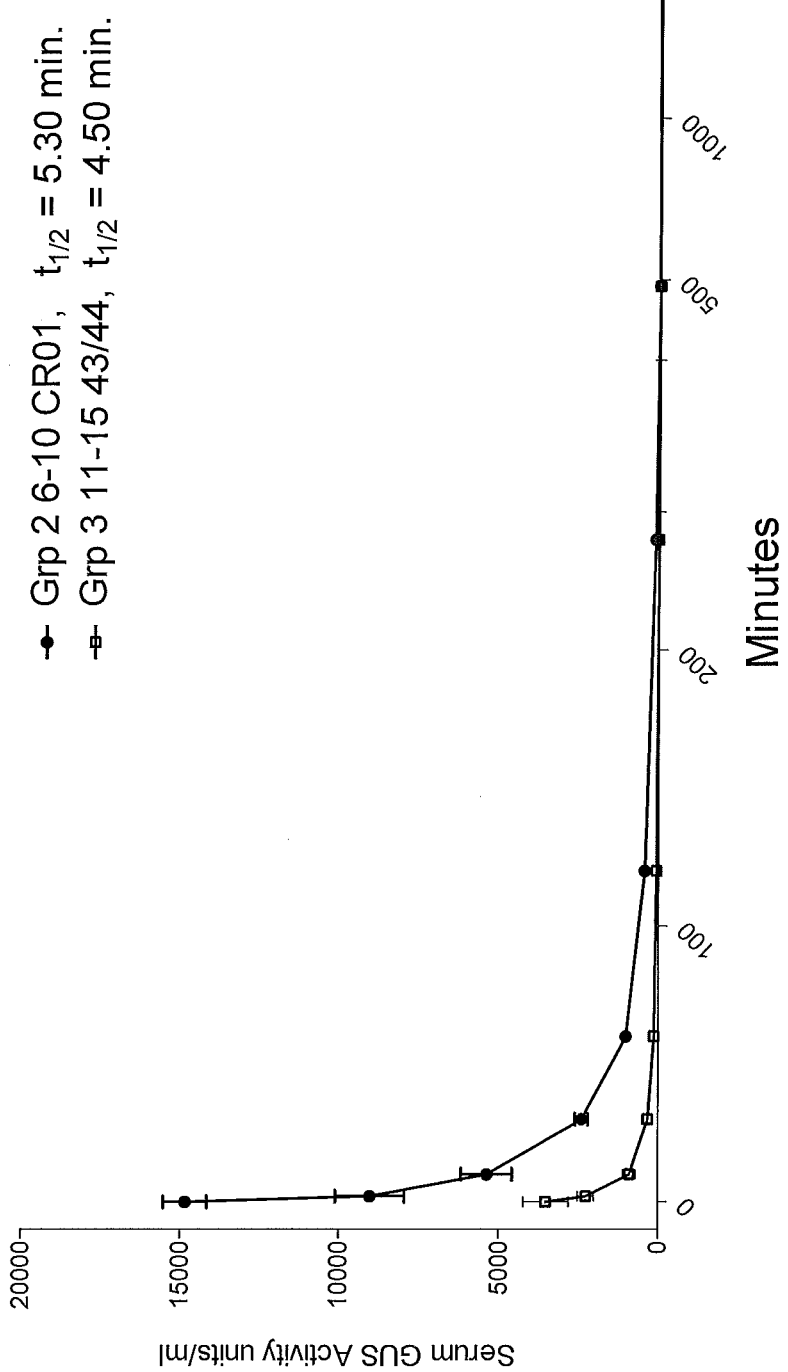
FIG. 2 is a plot showing only the post infusion clearance phase of GUS CR01 vs. GUS Lot 43/44 which was used to calculate the $t_{1/2}$ values. These differences in the rate of clearance are sufficient to result in higher serum levels of enzymes as shown in FIG. 1.
Figure 4:
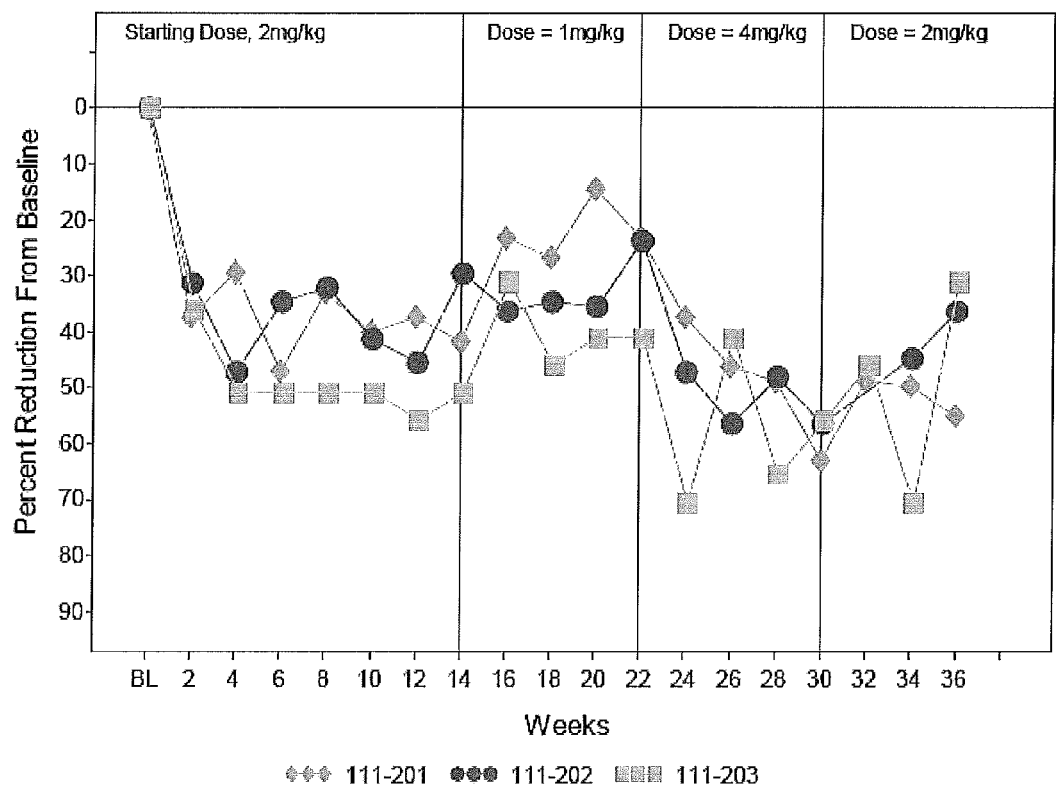
FIG. 4 is a plot showing the measurement of urinary glycosaminoglycan (uGAG) levels over 36 weeks in three subjects treated with recombinant human β-glucuronidase (rhGUS). A rapid and sustained dose-dependent reduction in uGAG levels was observed in subjects treated with rhGUS.

In FIG. 2, we present the post infusion clearance phase for both enzymes from which were calculated the $t_{1/2}$ values. GUS Lot 43/44 is cleared from the circulation with a $1^{st}$ phase $t_{1/2}$ of 4.50 minutes. In contrast, GUS CR01 is cleared at the slightly slower $t_{1/2}$ of 5.30 minutes. Raw clearance data was analyzed by a different method to re-calculate the $t_{1/2}$ values (FIG. 4 A and B). The Cmax (14800 for GUS CR01 vs 4300 for GUS lot 43/44) and the AUC-t (18700 vs 5580) are showing also a 3 fold higher for GUS (Table 5). The $t_{1/2}$ was calculated very differently as only the second phase was taken into account. For GUS CR01, the $2^{nd}$ phase $t_{1/2}$ is 1.1 hr and 0.967 hr for GUS lot 43/44 (Table 5).

TABLE 5

| Group | Animal | Cmax (Units/mL) | Tmax (h) | AUC0-t (h*Units/mL) | AUC0-inf (h*Units/mL) | Half-life (h) | Clearance (min*Units/mL)/(mg/kg) | Vz (Units/mL/mg/kg) |
|---|---|---|---|---|---|---|---|---|
| Grp 2 6-10 CR01 | 2-6 | 12900 | 0 | 15300 | 15500 | 2.05 | 2.19E−06 | 0.000389 |
| | 2-7 | 14200 | 0 | 16900 | 16900 | 0.794 | 2.01E−06 | 0.000138 |
| | 2-8 | 14200 | 0 | 18300 | 18400 | 0.926 | 1.84E−06 | 0.000148 |
| | 2-9 | 16700 | 0 | 22800 | 23000 | 1.03 | 1.47E−06 | 0.000132 |
| | 2-10 | 16000 | 0 | 20300 | 20300 | 0.67 | 1.66E−06 | 9.65E−05 |
| | Mean | 14800 | 0 | 18700 | 18800 | 1.1 | 1.84E−06 | 0.000181 |
| | CV % | 10.4 | | 15.7 | 15.7 | 50.5 | 15.3 | 65.4 |
| | Geometric Mean | 14800 | | 18500 | 18600 | 1.01 | 1.82E−06 | 0.000159 |
| Grp 3 11-15 43/44 | 3-11 | 4640 | 0 | 5380 | 5380 | 0.677 | 6.26E−06 | 0.000367 |
| | 3-12 | 7010 | 0.03 | 6940 | 6950 | 0.832 | 4.84E−06 | 0.000349 |
| | 3-13 | 4870 | 0 | 6220 | 6250 | 1.02 | 5.38E−06 | 0.000476 |
| | 3-14 | 2740 | 0.03 | 5420 | 5430 | 1.39 | 6.20E−06 | 0.000747 |
| | 3-15 | 2270 | 0 | 3970 | 3980 | 0.913 | 8.45E−06 | 0.000668 |
| | Mean | 4300 | 0.0133 | 5580 | 5600 | 0.967 | 6.23E−06 | 0.000521 |
| | CV % | 44 | 136.9 | 19.9 | 19.8 | 27.8 | 22.1 | 34.4 |
| | Geometric Mean | 3970 | | 5490 | 5510 | 0.939 | 6.11E−06 | 0.000497 |

Tissue Distribution of GUS CR01 vs. GUS Lot 43/44

In addition to clearance of the two enzymes, we assessed the tissue distribution of GUS CR01 compared to GUS Lot 43/44 in liver, spleen, heart, kidney, brain and lung. Tissue extracts prepared from each of these tissues were assayed for β-glucuronidase and protein as described in the methods. The results of the assays were expressed as units of β-glucuronidase activity/mg of tissue protein. The summary of these assays can be seen in FIG. 4. In each of the graphs of this figure, the total enzyme levels including the endogenous rat β-glucuronidase is shown on the left side. On the right side of each graph the average endogenous enzyme level has been subtracted from the total enzyme level. The average endogenous p-glucuronidase level from each tissue was calculated using values from all five rats from saline infused Group 1.

In each tissue, the level of GUS in rats infused with either GUS CR01 or GUS Lot 43/44 is higher than the saline infused rats. When the endogenous GUS levels are subtracted, it becomes apparent that rats infused with GUS CR01 contain GUS levels that are at least two times greater than rats infused with GUS Lot 43/44.

This study was designed to assess the β-glucuronidase pharmacokinetic and tissue distribution properties of GUS CR01 and GUS Lot 43/44. The current study determined that GUS CR01 was cleared from the circulation with a $1^{st}$ phase $t_{1/2}$ of 5.30 minutes, compared with a faster $t_{1/2}$ of 4.50 minutes for GUS Lot 43/44. The second phase $t_{1/2}$ is also a bit bigger for GUS CR01.

More significant differences between the 2 enzymes were demonstrated for Cmax, AUC-t and tissue distribution. The maximum concentration ($C_{max}$) of β-glucuronidase activity in the serum at the end of the two hour infusion period for GUS CR01 was 14,829 units/ml, 4.2 times the concentration of 3537 units/ml attained by GUS Lot 43/44. This increase in $C_{max}$ could be explained by the accumulation of the slower clearing enzyme to a higher concentration in the blood during the infusion period. AUC-t was also highly increased (more than 3 time) with GUS CR01 vs. GUS Lot 43/44 as represented in FIG. 1.

Figure 3:
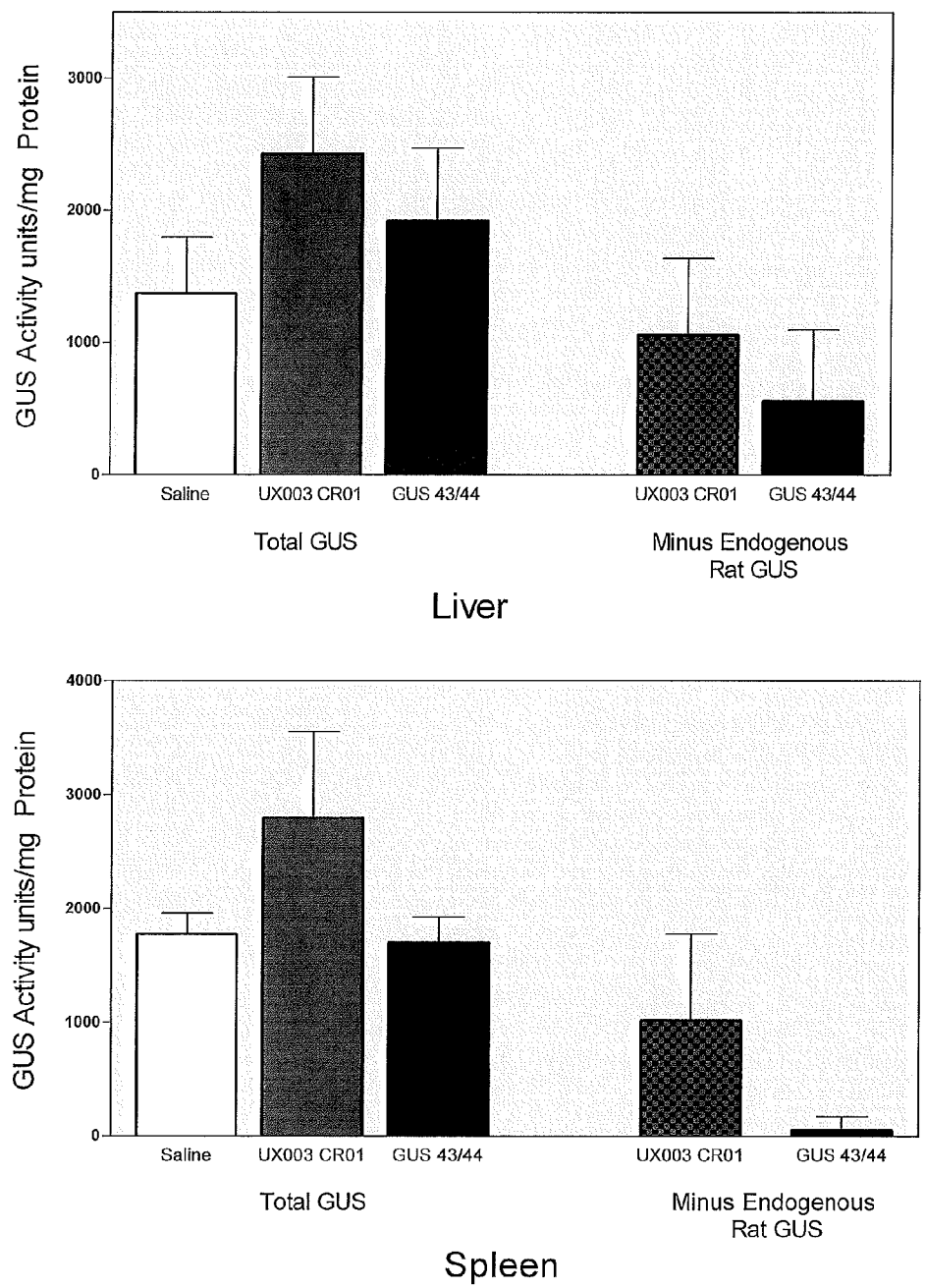
FIG. 3 is a series of plots showing tissue GUS levels for the pharmacokinetics study of GUS CR01 vs. GUS Lot 43/44. The tissue delivery and uptake of human β-glucuronidases is shown to be enhanced as the total uptake of sialylated human β-glucuronidases (CR01) is higher in all tissues than the lower sialylated enzyme (43-44). When the endogenous glucuronidase activity is substracted, the effective delivery of therapeutic human β-glucuronidases is increased 2 fold to almost 10 fold, an exceptional and surprising finding.

Last but not least, we observed that in all of the tissues tested that GUS CR01 was delivered to tissues at levels up to two times or greater than that of GUS Lot 43/44. Changing the clearance characteristics of a lysosomal enzyme from the circulation is known to have an effect on tissue distribution. It is conceivable that slowing the $t_{1/2}$ of GUS CR01 in the circulation could allow for a more efficient distribution of the enzyme to selected tissues. More importantly the changes in tissue distribution seem to correlate very well with the changes of Cmax and AUC-t. As can be seen in FIG. 3, the error bars are quite large, reflecting a large range of values obtained in the individual rats of each study group. Repeat β-glucuronidase assays in triplicate on selected tissues confirmed the original values leading us to believe that the wide range of values seen in these rats were real.

Previously, analysis of GUS CR01 has shown that whereas the level of mannose 6 phosphate and most other properties are quite similar between the 2 enzymes, the sialic acid content of GUS CR01 is 28 times that of GUS Lot 43/44 (1.1 mol/mol GUS monomer vs. 0.04 mol/mol GUS monomer). See Table 6.

TABLE 6

Characteristics of GUS CR01 and GUS Lot 43/44

| Characteristic/Assay | Units | GUS CR01 | GUS Lot 43/44 | GMP1 | GMP2 | GMP3* |
|---|---|---|---|---|---|---|
| Titer | mg/L | ~400 | ~50 | ~400 | ~400 | ~400 |
| pH | −log [H+] | 7.4 | 7.5 | 7.4 | 7.6 | 6.0 |
| Purity(Reducing SDS-PAGE) | % | 99.2 | >95.0 | 99.2 | 98.8 | 99.3 |
| Tetramer (SE-HPLC) | % | 97.7 | 99.0 | 98.4 | 98.6 | 99.1 |
| Molecular Weight Tetramer | Daltons | 290,249 | 300,000 | 300,000 | 300,000 | 300,000 |
| Mass Extinction Coefficient | $(mg/mL)^{-1} cm^{-1}$ | 2.08 | — | 2.0 | 2.0 | 2.1 |
| Charge Heterogeneity(IEF) | pH Range | comparable | 6.6-7.7 | comparable | comparable | comparable |
| M6P N-Glycan Analysis (Sum of Peaks 15-17) | mol-% | 14.2 | comparable | 14 | 14 | 12 |
| Sialic Acid Content | (moles/mole monomer) | 1.1 | 0.04 | 1.2 | 1.2 | 1.2 |
| Specific Activity | (MU/mg) | 3.6 | 3.70 | 3.9 | 3.7 | 3.5 |
| Cellular Uptake | Kuptake nM | 1.2-1.7 | 1.4 | 1.8 | 1.6 | 1.4 |
| Half-life in MPS7 Fibroblasts | Days 0-21 d | 20.0 | 18.9 | NA | NA | NA |
| | 5-21 d | 21.6 | 20.5 | | | |

*Monosaccharide analysis indicated that 71% of the galactose residues on GMP3 GUS are sialylated.

By putting together the data it is becoming quite apparent that the better tissue distribution of GUS CR01 demonstrated here is due to its increase in sialic acid content as sialic acid is well known to slow glycoproteins clearance from the circulation by mannose receptors located in the endothelial cells in the interior walls of the blood vessels. The combination of high sialic acid levels and high affinity mannose-6-phosphate moieties provides an optimal combination for reducing tissue uptake via other carbohydrate receptors due to the high sialic acid content, assuring higher concentrations in circulation and then achieving excellent tissue uptake in the target tissues due to the high affinity mannose-6-phosphate levels.

Example 3

Treatment of MPS VII Using Enzyme Replacement Therapy

The purpose of this example is to demonstrate that enzyme replacement therapy for mucopolysaccharidosis type VII (i.e., MPS VII; Sly's Syndrome) using recombinantly produced human β-glucuronidase (rhGUS) reduces lysosomal storage in a 36-week clinical study.

In this example, three subjects diagnosed with MPS VII were administered rhGUS with increased sialic acid content. Dosing was performed according to the following 36-week schedule:

Weeks 1-12: 2 mg/kg every other week;
Weeks 13-20: 1 mg/kg every other week;
Weeks 21-28: 4 mg/kg every other week; and
Weeks 29-36: 2 mg/kg every other week.

The safety and efficacy of rhGUS was assessed during the 36-week treatment schedule. The rhGUS compound appeared to be safe and well tolerated. Importantly, no serious adverse events were observed up to 36 weeks and there were no drug-related or hypersensitivity infusion-associated reactions in any of the three subjects.

Figure 5:
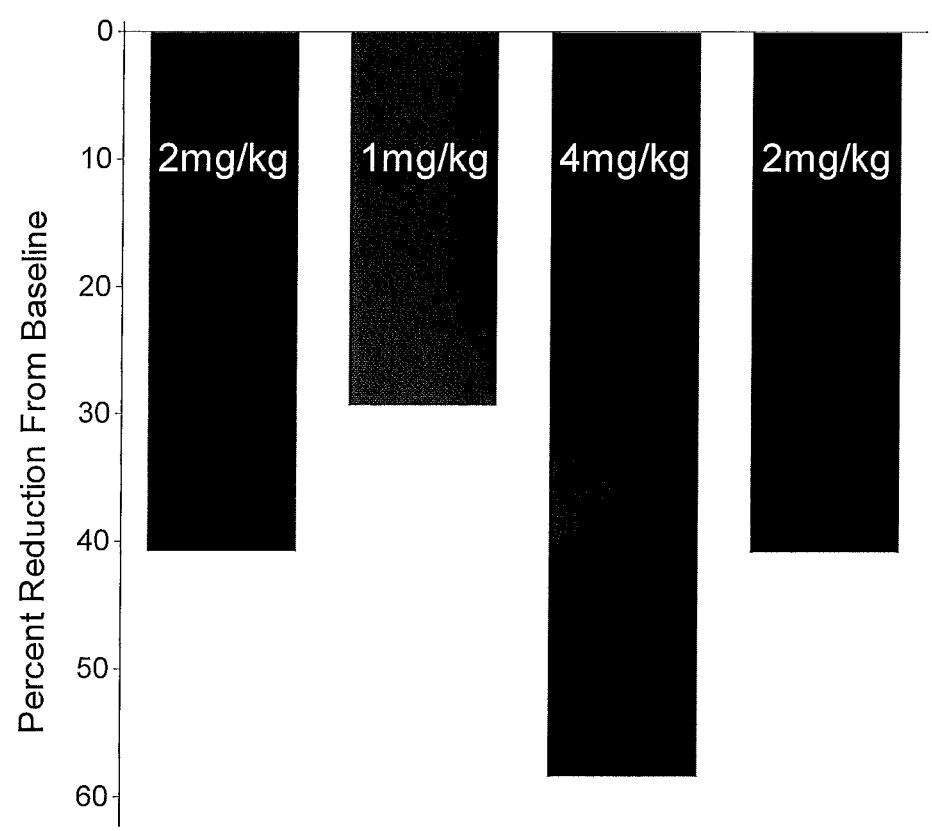
FIG. 5 illustrates the mean reduction in urinary glycosaminoglycan (uGAG) levels at the end of each dosing interval during a 36 week evaluation of three subjects treated with rhGUS. A 4 mg/kg QOW dose resulted in the greatest reduction in uGAG levels.

To measure efficacy, urinary and serum levels of glycosaminoglycans (GAGs) were first evaluated, as lysosomal accumulation of GAGs is a hallmark of GUS deficiency. A rapid and sustained dose-dependent reduction in urinary glycosaminoglycan (uGAG) was observed in subjects treated with rhGUS. See FIG. 4. The mean reduction in uGAG at the end of each dosing interval is shown in FIG. 5 and illustrates that a 4 mg/kg dose resulted in the greatest reduction of uGAG levels.

Figure 6:
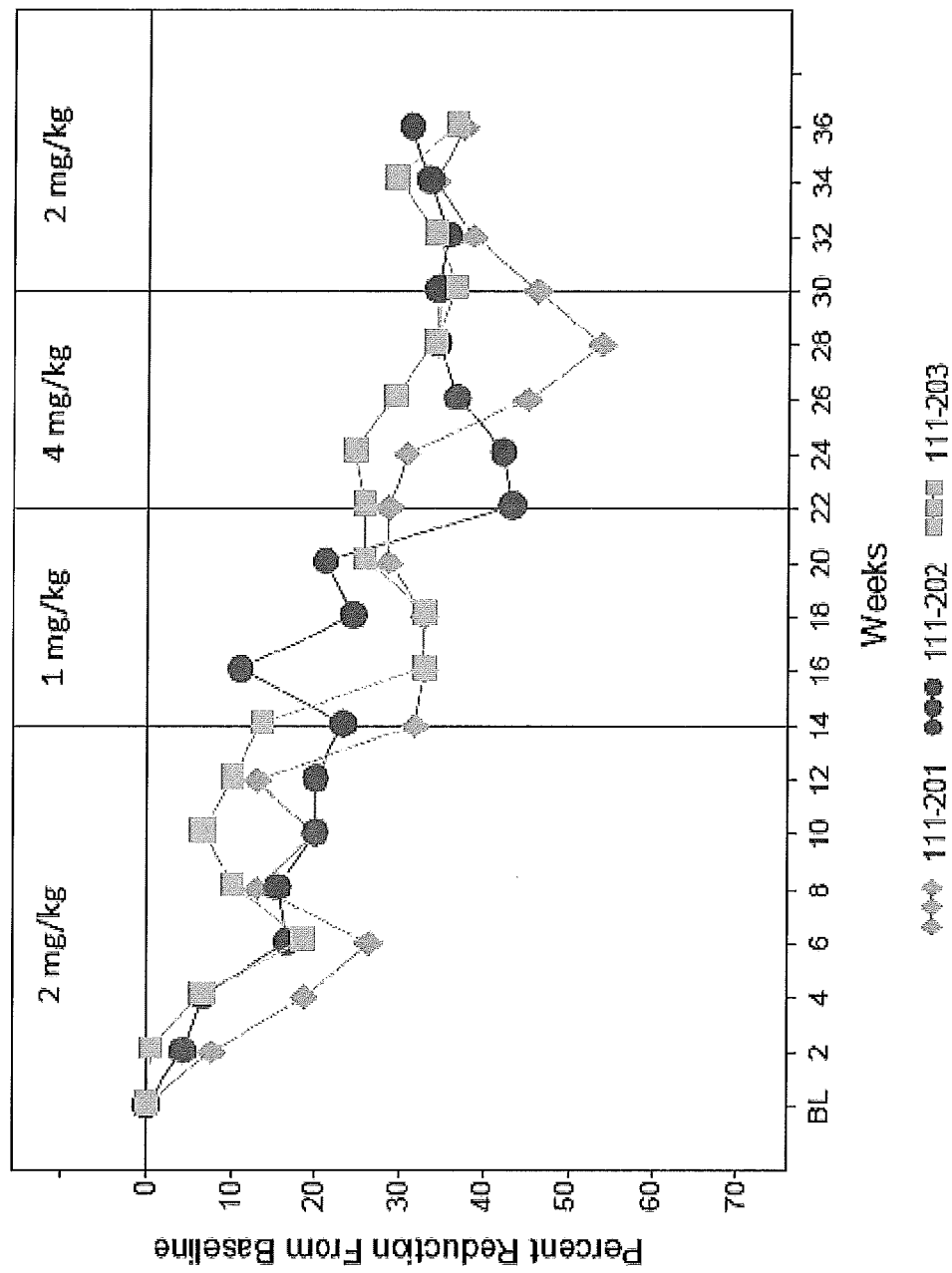
FIG. 6 is a plot showing the measurement of serum glycosaminoglycan (GAG) levels over 36 weeks in three subjects treated with rhGUS. Each subject demonstrated at least a 25% reduction in serum GAG levels at the end of the 36-week treatment schedule.

A progressive reduction in serum glycosaminoglycan (GAG) was also seen in all three subjects treated with rhGUS. Notably, each subject demonstrated at least a 25% reduction in serum GAG levels at the end of the 36-week treatment schedule. See FIG. 6.

Figure 7:
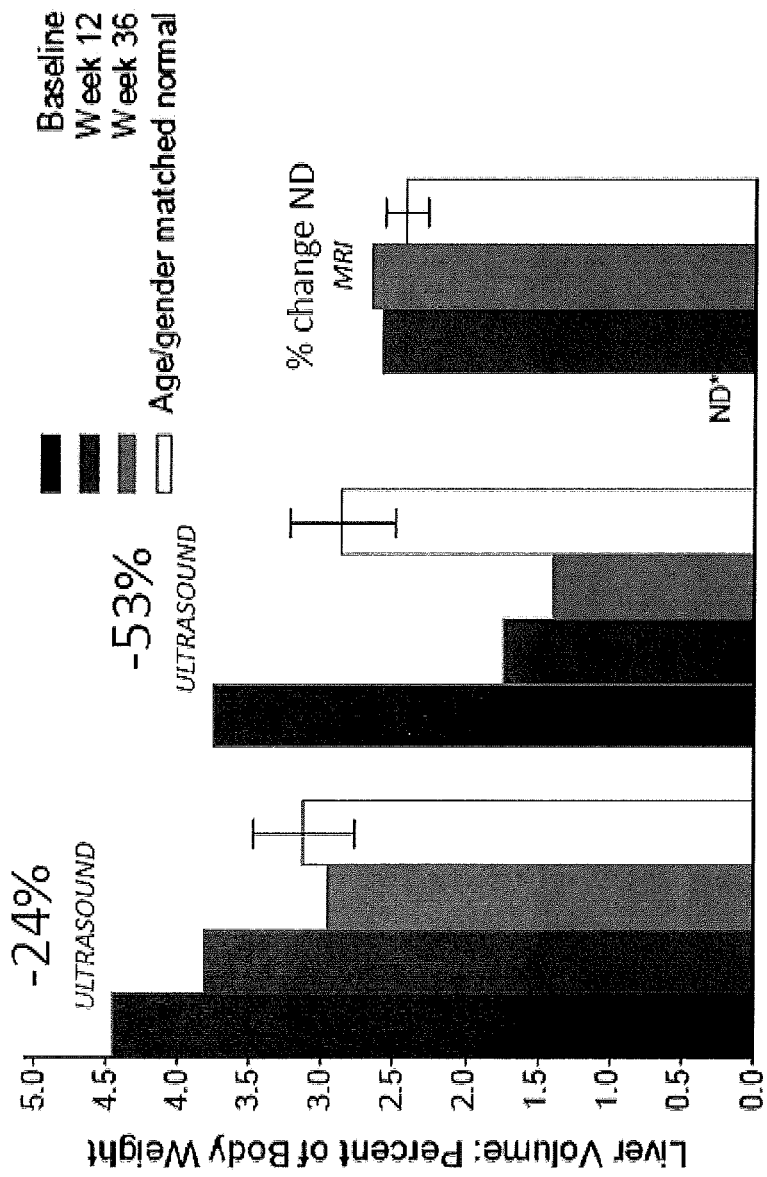
FIG. 7 is a plot showing the measurement of liver size in subjects treated with rhGUS. A significant reduction in hepatomegaly resulting from the 36 week treatment protocol was observed.

Lastly, liver size was evaluated in subjects treated with rhGUS, as enlarged liver size is frequently observed in patients suffering from MPS VII. There was a significant reduction in hepatomegaly resulting from the 36-week treatment protocol. See FIG. 7.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings.

---

What is claimed is:

1. A method of treating a lysosomal storage disorder in a subject in need thereof, comprising administering to the subject a therapeutically effective amount of a composition comprising a recombinant glycoprotein, wherein the recombinant glycoprotein is human β-glucuronidase and has a sialylation content of at least 0.7 mol/mol of the recombinant glycoprotein.

2. The method of claim 1, wherein the subject is a human.

3. The method of claim 1, wherein the lysosomal storage disorder is mucopolysaccharidosis type 7.

4. The method of claim 1, wherein the recombinant human β-glucuronidase is administered at a dose of at least about 0.5 mg/kg.

5. The method of claim 1, wherein the recombinant human β-glucuronidase is administered at a dose of about 1 mg/kg to about 8 mg/kg.

6. The method of claim 1, wherein the recombinant human β-glucuronidase is administered at a dose of about 2 mg/kg to about 6 mg/kg.

7. The method of claim 1, wherein the recombinant human β-glucuronidase is administered at a dose of about 4 mg/kg.

8. The method of claim 1, wherein the recombinant human β-glucuronidase is administered weekly.

9. The method of claim 1, wherein the recombinant human β-glucuronidase is administered every other week.

10. The method of claim 1, wherein the recombinant human β-glucuronidase is administered intravenously.

11. The method of claim 1, wherein the recombinant human β-glucuronidase is administered by continuous infusion.

12. The method of claim 1, wherein the recombinant human β-glucuronidase is administered concurrently with or following antihistamine therapy.

* * * * *

SEQUENCE LISTING

```
<160> NUMBER OF SEQ ID NOS: 1

<210> SEQ ID NO 1
<211> LENGTH: 629
<212> TYPE: PRT
<213> ORGANISM: Artificial Sequence
<220> FEATURE:
<223> OTHER INFORMATION: recombinant human beta-glucuronidase

<400> SEQUENCE: 1

Leu Gln Gly Gly Met Leu Tyr Pro Gln Glu Ser Pro Ser Arg Glu Cys
1               5                   10                  15

Lys Glu Leu Asp Gly Leu Trp Ser Phe Arg Ala Asp Phe Ser Asp Asn
            20                  25                  30

Arg Arg Arg Gly Phe Glu Glu Gln Trp Tyr Arg Arg Pro Leu Trp Glu
        35                  40                  45

Ser Gly Pro Thr Val Asp Met Pro Val Pro Ser Ser Phe Asn Asp Ile
    50                  55                  60

Ser Gln Asp Trp Arg Leu Arg His Phe Val Gly Trp Val Trp Tyr Glu
65                  70                  75                  80

Arg Glu Val Ile Leu Pro Glu Arg Trp Thr Gln Asp Leu Arg Thr Arg
                85                  90                  95

Val Val Leu Arg Ile Gly Ser Ala His Ser Tyr Ala Ile Val Trp Val
```

```
              100                 105                 110
Asn Gly Val Asp Thr Leu Glu His Glu Gly Gly Tyr Leu Pro Phe Glu
            115                 120                 125
Ala Asp Ile Ser Asn Leu Val Gln Val Gly Pro Leu Pro Ser Arg Leu
            130                 135                 140
Arg Ile Thr Ile Ala Ile Asn Asn Thr Leu Thr Pro Thr Thr Leu Pro
145                 150                 155                 160
Pro Gly Thr Ile Gln Tyr Leu Thr Asp Thr Ser Lys Tyr Pro Lys Gly
            165                 170                 175
Tyr Phe Val Gln Asn Thr Tyr Phe Asp Phe Phe Asn Tyr Ala Gly Leu
            180                 185                 190
Gln Arg Ser Val Leu Leu Tyr Thr Thr Pro Thr Thr Tyr Ile Asp Asp
            195                 200                 205
Ile Thr Val Thr Thr Ser Val Glu Gln Asp Ser Gly Leu Val Asn Tyr
210                 215                 220
Gln Ile Ser Val Lys Gly Ser Asn Leu Phe Lys Leu Glu Val Arg Leu
225                 230                 235                 240
Leu Asp Ala Glu Asn Lys Val Val Ala Asn Gly Thr Gly Thr Gln Gly
            245                 250                 255
Gln Leu Lys Val Pro Gly Val Ser Leu Trp Trp Pro Tyr Leu Met His
            260                 265                 270
Glu Arg Pro Ala Tyr Leu Tyr Ser Leu Glu Val Gln Leu Thr Ala Gln
            275                 280                 285
Thr Ser Leu Gly Pro Val Ser Asp Phe Tyr Thr Leu Pro Val Gly Ile
            290                 295                 300
Arg Thr Val Ala Val Thr Lys Ser Gln Phe Leu Ile Asn Gly Lys Pro
305                 310                 315                 320
Phe Tyr Phe His Gly Val Asn Lys His Glu Asp Ala Asp Ile Arg Gly
            325                 330                 335
Lys Gly Phe Asp Trp Pro Leu Leu Val Lys Asp Phe Asn Leu Leu Arg
            340                 345                 350
Trp Leu Gly Ala Asn Ala Phe Arg Thr Ser His Tyr Pro Tyr Ala Glu
            355                 360                 365
Glu Val Met Gln Met Cys Asp Arg Tyr Gly Ile Val Val Ile Asp Glu
            370                 375                 380
Cys Pro Gly Val Gly Leu Ala Leu Pro Gln Phe Phe Asn Asn Val Ser
385                 390                 395                 400
Leu His His His Met Gln Val Met Glu Glu Val Val Arg Arg Asp Lys
            405                 410                 415
Asn His Pro Ala Val Val Met Trp Ser Val Ala Asn Glu Pro Ala Ser
            420                 425                 430
His Leu Glu Ser Ala Gly Tyr Tyr Leu Lys Met Val Ile Ala His Thr
            435                 440                 445
Lys Ser Leu Asp Pro Ser Arg Pro Val Thr Phe Val Ser Asn Ser Asn
            450                 455                 460
Tyr Ala Ala Asp Lys Gly Ala Pro Tyr Val Asp Val Ile Cys Leu Asn
465                 470                 475                 480
Ser Tyr Tyr Ser Trp Tyr His Asp Tyr Gly His Leu Glu Leu Ile Gln
            485                 490                 495
Leu Gln Leu Ala Thr Gln Phe Glu Asn Trp Tyr Lys Lys Tyr Gln Lys
            500                 505                 510
Pro Ile Ile Gln Ser Glu Tyr Gly Ala Glu Thr Ile Ala Gly Phe His
            515                 520                 525
```

```
Gln Asp Pro Pro Leu Met Phe Thr Glu Glu Tyr Gln Lys Ser Leu Leu
    530                 535                 540

Glu Gln Tyr His Leu Gly Leu Asp Gln Lys Arg Arg Lys Tyr Val Val
545                 550                 555                 560

Gly Glu Leu Ile Trp Asn Phe Ala Asp Phe Met Thr Glu Gln Ser Pro
                565                 570                 575

Thr Arg Val Leu Gly Asn Lys Lys Gly Ile Phe Thr Arg Gln Arg Gln
            580                 585                 590

Pro Lys Ser Ala Ala Phe Leu Leu Arg Glu Arg Tyr Trp Lys Ile Ala
        595                 600                 605

Asn Glu Thr Arg Tyr Pro His Ser Val Ala Lys Ser Gln Cys Leu Glu
    610                 615                 620

Asn Ser Leu Phe Thr
625
```